United States Patent
Mitts et al.

(10) Patent No.: US 9,867,804 B2
(45) Date of Patent: *Jan. 16, 2018

(54) SODIUM ASCORBATE STIMULATION OF ELASTOGENESIS

(71) Applicants: HUMAN MATRIX SCIENCES, LLC, Visalia, CA (US); THE HOSPITAL FOR SICK CHILDREN, Toronto (CA)

(72) Inventors: Thomas F. Mitts, Visalia, CA (US); Aleksander Hinek, Toronto (CA); Hyunjun Jonathan Kim, Toronto (CA)

(73) Assignees: Human Matrix Sciences, LLC, Visalia, CA (US); The Hospital for Sick Children, Toronto, Ontario (CA)

( * ) Notice: Subject to any disclaimer, the term of this patent is extended or adjusted under 35 U.S.C. 154(b) by 5 days.

This patent is subject to a terminal disclaimer.

(21) Appl. No.: 15/195,011

(22) Filed: Jun. 28, 2016

(65) Prior Publication Data

US 2016/0303071 A1    Oct. 20, 2016

Related U.S. Application Data

(63) Continuation of application No. 13/745,393, filed on Jan. 18, 2013, now Pat. No. 9,387,194.

(60) Provisional application No. 61/587,864, filed on Jan. 18, 2012.

(51) Int. Cl.
| | |
|---|---|
| A61K 31/375 | (2006.01) |
| A61K 31/221 | (2006.01) |
| A61K 8/42 | (2006.01) |
| A61K 45/06 | (2006.01) |
| A61K 8/67 | (2006.01) |
| A61Q 19/08 | (2006.01) |

(52) U.S. Cl.
CPC .............. *A61K 31/375* (2013.01); *A61K 8/42* (2013.01); *A61K 8/676* (2013.01); *A61K 31/221* (2013.01); *A61K 45/06* (2013.01); *A61Q 19/08* (2013.01)

(58) Field of Classification Search
IPC ................... A61K 31/375,31/221, 8/42, 8/676
See application file for complete search history.

(56) References Cited

U.S. PATENT DOCUMENTS

| | | | |
|---|---|---|---|
| 7,560,430 B2 | 7/2009 | Mitts et al. | |
| 7,566,693 B2 | 7/2009 | Jimenez et al. | |
| 7,666,829 B2 | 2/2010 | Mitts et al. | |
| 7,723,308 B2 | 5/2010 | Jimenez et al. | |
| 7,745,225 B2 | 6/2010 | Mitts et al. | |
| 7,803,522 B2 | 9/2010 | Jimenez et al. | |
| 8,114,829 B2 | 2/2012 | Jimenez et al. | |
| 8,148,327 B2 | 4/2012 | Mitts et al. | |
| 2003/0068297 A1* | 4/2003 | Jain .......................... A61K 8/64 424/85.1 |
| 2009/0110709 A1 | 4/2009 | Mitts et al. | |
| 2009/0281044 A1 | 11/2009 | Mitts et al. | |
| 2010/0247454 A1 | 9/2010 | Mitts et al. | |
| 2010/0331252 A1* | 12/2010 | Hamrick .............. A61K 9/0019 514/8.9 |
| 2011/0081322 A1 | 4/2011 | Jimenez et al. | |
| 2011/0165176 A1 | 7/2011 | Hinek et al. | |
| 2011/0237516 A1 | 9/2011 | Jimenez et al. | |
| 2012/0116346 A1 | 5/2012 | Mitts et al. | |
| 2012/0195914 A1 | 8/2012 | Mitts et al. | |
| 2013/0065835 A1 | 3/2013 | Mitts et al. | |
| 2013/0184199 A1 | 7/2013 | Mitts et al. | |
| 2013/0184337 A1 | 7/2013 | Mitts et al. | |

FOREIGN PATENT DOCUMENTS

| | | | |
|---|---|---|---|
| CA | 2803240 A1 | 7/2013 | |
| WO | WO 2004/094369 A2 | 11/2004 | |
| WO | WO 2012037212 | * 3/2012 | |

OTHER PUBLICATIONS

Davidson et al. (The J. of Bio. Chemistry 272(1) 345-352 ).*
Sears et al. PNAS 2008; 105(50), 19898-19903.*
Banker et al. "Modern Pharmaceutics" 1979, Marcel Dekker, Inc., New York (TOC).
Geesin et al. "Ascorbic Acid Specifically Increases Type I and Type III Procollagen Messenger RNA Levels in Human Skin Fibroblasts" 1988, J. Invest. Dermatol. 90:420-424.
Goodman et al. "The Pharmaceutical Basis of Therapeutics, 6th ed." 1980, MacMillan Publishing Co., New York (TOC).
Hyunjun Kim "Sodium Ascorbate as a Potent Stimulator of Elastic Fiber Production" 2011, Univ. of Toronto 1-98.
Kim "Sodium Ascorbate as a Potent Stimulator of Elastic Fiber Production" (Thesis) 2011.
Liu et al. "Prolyl Hydroxylase Inhibitor Dimethyloxalylglycine Enhances Mesenchymal Stem Cell Survival" 2009, J. Cell. Biochem. 106:903-911.
McDonald et al. "Role of Fibronectin in Collagen Deposition: Fab' to the Gelatin-binding Domain of Fibronectin Inhibits Both Fibronectin and Collagen Organization in Fibroblast Extracellular Matrix" Feb. 1, 1982, J. Cell Biology 92:485-492.
Shi et al. "Insulin Induces Production of New Elastin in Cultures of Human Aortic Smooth Muscle Cells" Feb. 2, 2012, Amer. J. Pathol. 180(2):715-726.
Shi et al. "Insulin Promotes Elastin production in cultures of Human Aortic Smooth Muscle Cells and Skin Fibroblasts" 2011, Inst. Med. Sci. Univ. Toronto, 39 pages.

* cited by examiner

Primary Examiner — Shirley V Gembeh
(74) Attorney, Agent, or Firm — Pepper Hamilton LLP

(57) ABSTRACT

Embodiments provide methods for using ascorbate for the stimulation of production of elastic fibers by cells.

6 Claims, 22 Drawing Sheets
(10 of 22 Drawing Sheet(s) Filed in Color)

20 Hours

Cultures of Fibroblasts from Dermal Stretch-Marks
Immuno-localization of Collagen I

Immuno-localization of Elastin

SODIUM ASCORBATE STIMULATION OF ELASTOGENESIS

CROSS-REFERENCE TO RELATED APPLICATIONS

This application is a continuation application of U.S. application Ser. No. 13/745,393 filed Jan. 18, 2013, which claims the benefit of U.S. Provisional Application No. 61/587,864 filed Jan. 18, 2012, incorporated herein by reference in their entirety.

GOVERNMENT INTERESTS

This invention was partially funded by a grant from the Canadian Institute of Health Research (grant No. PG 13920) and by the Heart and Stroke Foundation of Ontario (grant No. NA 4381).

BRIEF SUMMARY OF THE INVENTION

Embodiments presented herein are useful for stimulating elastic fiber production by cells through the use of ascorbate anions.

In one embodiment, an ascorbic acid salt, sodium ascorbate, stimulates production of both collagen and elastic fibers in cultures of fibroblasts derived from normal and pathologic human skin, fat tissue, and myocardium, as well as by human aortic smooth muscle cells. The intracellular influx of SA, facilitated via the probenecid-sensitive transporter, associates with a significant reduction of reactive oxygen species. This, in a short time, contributes to better preservation of newly synthesized tropoelastins, while also creating permissive conditions for activation of c-Src tyrosine kinase, which facilitates the IGF-1-induced phosphorylation of IGF-1 receptor that triggers a signaling pathway leading to activation of the elastin gene expression, and a final enhancement of elastin deposition.

In various embodiments, SA can be used to selectively stimulate elastic fiber deposition by cells such as those present in dermal scars, the aorta, or the heart. In certain embodiments, SA may be applied in combination with factors interfering with collagen deposition (for example, proline-hydroxylase inhibitor or mineralo-corticosteroid receptors inhibitors: spironolactone and eplerenone).

In various other embodiments, SA can be used as a potent stimulator of collagen and elastin production. In such embodiments, SA is useful for the treatment of wrinkled and stretched skin, and for bioengineering of resilient dermal and arterial constructs.

Embodiments further comprise methods for administering an effective amount of SA to a skin area to at least treat, or otherwise decrease wrinkles and stretch marks. In such embodiments, SA may be administered, for example, by injection or topical administration, and may be administered with a pharmaceutically acceptable carrier, diluent or excipient.

Additional embodiments comprise methods for including an effective amount of SA during bioengineered growth of dermal and arterial cells to form artificial constructs thereof.

Further embodiments are drawn to inclusion of SA into therapeutic combinations aimed at stimulation of non-fibrotic remodeling of the metabolically injured and post-infarct hearts, prevention of arterial occlusions, and prevention of development of rigid dermal scars.

Embodiments may include methods for administering an effective amount of SA to injured heart areas to stimulate remodeling of the injured areas. In various other embodiments, SA may be administered, for example, by injection, via a catheter, or by other known methods, and may be administered with a pharmaceutically acceptable carrier, diluent or excipient.

Other embodiments include methods for administering an effective amount of SA to arterial sites to prevent, or decrease occurrence of occlusions. As such, SA may be administered, for example, by injection, via a catheter, or by other known methods, and may be administered with a pharmaceutically acceptable carrier, diluent or excipient.

Yet further embodiments include methods for administering an effective amount of SA to injured skin areas to prevent, or at least decrease dermal scars. As such, SA may be administered, for example, by injection or topical administration, and may be administered with a pharmaceutically acceptable carrier, diluent or excipient.

DESCRIPTION OF DRAWINGS

The file of this patent contains at least one photograph or drawing executed in color. Copies of this patent with color drawings or photographs will be provided by the Office upon request and payment of necessary fee.

For a fuller understanding of the nature and advantages of the present invention, reference should be made to the following detailed description taken in connection with the accompanying drawings.

DETAILED DESCRIPTION

Figure 1A:
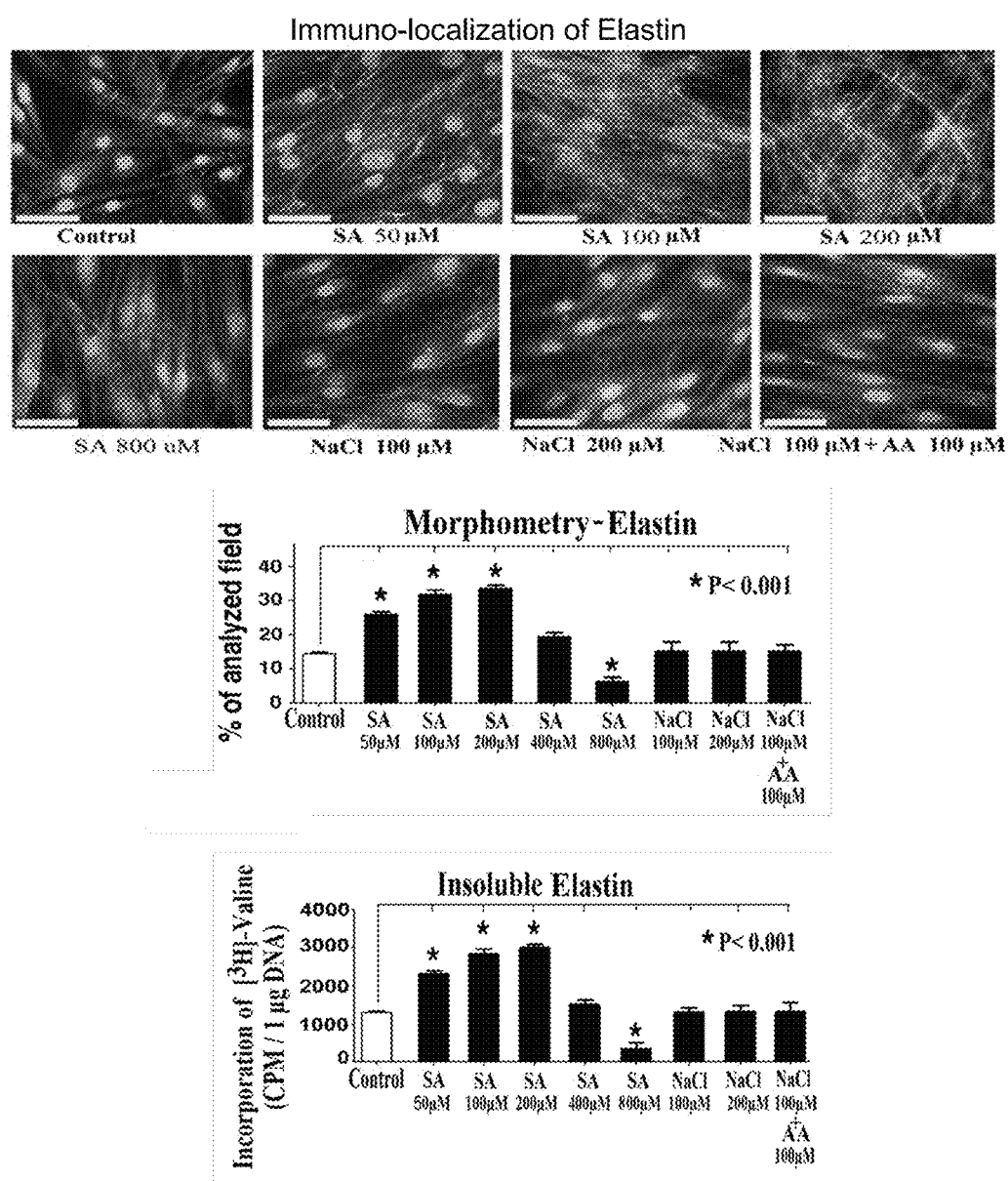
FIGS. 1A-1B. Representative micrographs depicting immuno-detected elastin and collagen fibers, followed by the results of their morphometric evaluation and quantification of the metabolically-labeled insoluble elastin in 24 hour-old cultures of normal dermal fibroblasts maintained in the presence of 5% FBS. Cell nuclei stained with red propidium iodide. (Scale bars=15 μm). (A) While treatments with 50 μM to 200 μM SA upregulate production of elastic fibers, treatment with 800 μM SA inhibits elastogenesis. Treatment with 100-200 μM NaCl or with combination of 100 μM NaCl and 100 μM AA do not induce elastogenesis. (B) 100 μM SA induces a more potent upregulation in collagen fibers deposition than 100 μM AA, which also completely inhibits elastic fiber formation. Addition of proline hydroxylase inhibitor (DMOG) to SA-treated cultures inhibits the deposition of collagen fibers, but does not diminish the elastogenic effect of SA. Results are based on data obtained from three individual experiments, in which quadruplicate cultures were exposed to indicated treatments. Results from all experimental groups were statistically evaluated and finally expressed as mean±SD.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

Contrary to the observed effects of Vitamin C (L-ascorbic acid) increasing collagen deposition in cells and inhibiting elastogenesis, salts of L-ascorbic acid (SA) applied in 50-200 μM concentrations are disclosed herein to stimulate production of both collagen and elastic fibers in cultures of fibroblasts derived from normal human skin and dermal fat, as well as in cultured explants of normal and stretch-marked human skin. Moreover, SA applied in combination with a proline hydroxylase inhibitor exclusively induces deposition of elastic fibers in cultured explants of dermal scars. As disclosed herein, SA stimulates elastogenesis after intracellular influx of non-oxidized ascorbate anions that scavenge reactive oxygen species (ROS). Such down-regulation of ROS contributes to the activation of c-Src tyrosine kinase and the consecutive enhancement of IGF-1-induced phosphorylation of the IGF-1 receptor that triggers a signaling pathway leading to the activation of elastin gene expression and subsequent deposition of elastic fibers. Thus, in various embodiments, SA can be used as a potent stimulator of collagen and elastin production in the treatment of wrinkled and stretch-marked skin, as well as be included with therapeutic combinations of collagenogenesis inhibitors to prevent formation of dermal scars. Similarly, SA can be used in low dose regimens to preferentially stimulate cellular elastogenesis over collagen production.

It must be noted that as used herein, and in the appended claims, the singular forms "a," "an," and "the" include plural reference unless the context clearly dictates otherwise. Thus, for example, reference to a "fibroblast" is a reference to one or more fibroblasts and equivalents thereof known to those skilled in the art.

As used herein, all claimed numeric terms are to be read as being preceded by the term, "about," which means plus or minus 10% of the numerical value of the number with which it is being used. Therefore, as an example, a claim to "50%" means "about 50%" and encompasses the range of 45%-55%.

"Administering," or conjugates thereof, when used in conjunction with a therapeutic, means to administer a therapeutic directly into or onto a target tissue, or to administer a therapeutic to a patient whereby the therapeutic positively impacts the tissue to which it is targeted. "Administering" a composition may be accomplished by any mode including parenteral administration including injection, oral administration, topical administration, pleural infusion, pericardial infusion, or by any other method known in the art including for example electrical deposition (e.g., ionotophoresis) and ultrasound (e.g., sonophoresis). In certain embodiments, the compositions described herein may be administered in combination with another form of therapy, including for example radiation therapy, infrared therapy, ultrasound therapy, or any other therapy know in the art or described herein.

In certain embodiments, the compositions may be combined with a carrier. A "carrier" as used herein may include, but is not limited to, an irrigation solution, antiseptic solution, other solution time released composition, elution composition, bandage, dressing, colloid suspension (e.g., a cream, gel, or salve) internal or external dissolvable sutures, dissolvable beads, dissolvable sponges and/or other materials or compositions known now or hereafter to a person of ordinary skill in the art.

The term "animal" as used herein includes, but is not limited to, humans and non-human vertebrates, such as wild, domestic, and farm animals.

The term "improves," or conjugates thereof, are used to convey that the present invention changes either the appearance, form, characteristics, function and/or the physical attributes of the material to which it is being provided, applied or administered. The changes may be demonstrated by any of the following, alone or in combination: enhanced production of elastin, increased elasticity of the tissue, reduced scar tissue formation or any other such improvement recognized in the art or described herein.

The term "inhibiting," or conjugates thereof, includes the administration of a compound of the present invention to prevent the onset of the symptoms, alleviating the symptoms, or eliminating the disease, condition or disorder.

By "pharmaceutically acceptable," it is meant that the carrier, diluent or excipient must be compatible with the other ingredients of the formulation and not deleterious to the recipient thereof. By "excipient," it is meant any inert or otherwise non-active ingredient, which can be added to the active ingredient which may improve the overall composition's properties, such as improving shelf-life, improving retention time at the application site, improving flowability, improving consumer acceptance, et alia.

As used herein, the salts of ascorbic acid (SA) are those wherein a hydrogen ion generated by dissociation of H can be substituted by a positive ion such as a metal ion, ammonium ion and the like to form a salt. Such salts are also included in the scope of the disclosure and include includes inorganic salts and organic salts. Inorganic salts include salts of an alkali metal such as, but not limited to, lithium, sodium and potassium, salts of an alkaline earth metal such as, but not limited to calcium and magnesium, ammonium salt and the like. Organic salts include a diethanolamine salt, triethanolamine salt, basic amino acid salts such as, but not limited to arginine, lysine, carnosine, and glutathione, or other organic salt such as, but not limited to glucosamine, nicotinamide, niacin, niacinamide, allantoin, creatine, creatinine, chitosan and the like. Formation of such salts can be carried out by the same method as for known salt formation methods such as neutralization of an aqueous solution of an ascorbic acid derivative with a basic substance.

As used herein, the term "therapeutic" means an agent utilized to treat, combat, ameliorate, prevent or improve an unwanted condition or disease of a patient.

A "therapeutically effective amount" or "effective amount" of a composition is a predetermined amount calculated to achieve the desired effect, i.e., to increase production of elastin or the deposition of elastic fibers. For example, a therapeutic effect may be demonstrated by increased elastogenesis, increased cellular proliferation, increased digestion or resorption of scar material, reduction of symptoms and sequellae as well as any other therapeutic effect known in the art. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, the physical characteristics of the patient (height, weight, etc.), and the condition being treated. It will be understood that the effective amount administered will be determined by the physician in light of the relevant circumstances, including the condition to be treated, the choice of compound to be administered, and the chosen route of administration, and therefore, the dosage ranges provided are not intended to limit the scope of the invention in any way. A "therapeutically effective amount" of compound of this invention is typically an amount such that when it is administered in a physiologically tolerable excipient composition, it is sufficient to achieve an effective systemic concentration or local concentration in the tissue.

In certain embodiments, the local cellular concentration of SA is in the range of 50-200 µM/L. Those of skill in the art recognize that such a concentration is easily convertible among equivalents. For example, where the molecular weight of sodium ascorbate is 198.11 MW, the solute mass in a 1 µM/L solution is 198.11 µM/L. Similarly, the use of the volume in the denominator is not necessary to describe the molarity of a solution. Therefore, as in the above example, a 1 µM solution of sodium ascorbate would comprise ascorbate at a ratio of 198.11 µg/L of water.

As such, the concentrations of an ascorbate anion necessary to produce elastogenesis can be 0.01 µM, 0.05 µM, 0.1 µM, 0.2 µM, 0.3 µM, 0.4 µM, 0.5 µM, 0.6 µM, 0.7 µM, 0.8 µM, 0.9 µM, 1.0 µM, 2.0 µM, 3.0 µM, 4.0 µM, 5.0 µM, 6.0 µM, 7.0 µM, 8.0 µM, 9.0 µM, 10.0 µM, 20 µM, 30 µM, 40 µM, 50 µM, 60 µM, 70 µM, 80 µM, 90 µM, 100 µM, 200 µM or higher. Those of skill in the art recognize that distribution of ascorbate in the body and throughout the tissues is not uniform, so that an in situ concentration of 50-200 µM inducing elastogenesis locally may be independent of the systemic concentration or dose. As such, it is contemplated that systemic administration of ascorbate, for example, can be adjusted to target individual classes of cells, individual tissues, and individual organs depending on the type of disease and symptoms of that disease. It is also contemplated that ascorbate can be delivered locally to a site such as skin in need of elastogenesis so that the concentration in situ is 50-200 µM.

In certain embodiments, ascorbate may interact with cells so as not to significantly induce collagen type I and fibronectin production or cause cellular proliferation. In certain embodiments, therapeutically active concentrations of ascorbate required to activate elastogenesis are lower than those used in other applications and treatments. In certain embodiments, the dosage window balancing such effects is termed "low dose" ascorbate treatment and comprises a dosage creating a concentration of ascorbate of 50-200 µM locally. Such local concentrations can be achieved by any means known in the art including deposition injection, topical administration, perfusion and others. As such, it is also contemplated in the disclosure that when ascorbate is administered to induce elastogenesis, the dosages are adjusted so as to avoid stimulation any concomitant effects opposing the elastogenic action of the ascorbate, such as for example, avoiding production of collagen type I and fibronectin or stimulating cellular proliferation.

The term "treat" as used herein, refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects.

Thus, methods of treatment are disclosed herein which involve the simultaneous topical application, or intra-lesion injection, of therapeutic amounts of each of disclosed compounds for treatment of dermal scars. It is now common to use fibroblasts, isolated from human skin, in the manufacture of artificial skin to temporarily cover chemically or thermally damaged skin, or replace skin destroyed by ischemia or infection. While the use of autologous fibroblasts obtained from the injured patient can be one solution, the harvesting of large numbers of dermal fibroblasts is not always possible. Thus, the harvesting of a larger number of ECM-producing fibroblasts from the fat tissue by liposuction emerged as a safe and more feasible alternative. In fact, intra dermal injection of fat-derived fibroblasts capable of resuming the production of collagen and fibronectin has already been used to regenerate damaged skin. The therapeutic effect of locally-injected fat-derived fibroblasts has also been reported in the healing of difficult wounds. However to date the elastogenic potential of these cells has not been evaluated. The disclosed embodiments that treatment of fat tissue fibroblasts with micromolar concentrations of SA, also boosts the production of elastin, further encourages methods of using these SA-stimulated cells for regeneration of damaged skin, and also encourages methods for use of the SA stimulated cells for the bioengineering of more elastic skin replacements.

Vascular smooth muscle cells (SMCs) are the main types of cells residing in the tunica media of arteries and veins. During normal embryonic development, and in the neonatal period, the SMCs are responsible for the deposition of extracellular matrix, rich in elastic fibers and lamellae that are mostly responsible for the resiliency of vascular walls and for carrying the pulsation flow of blood through the aorta and large arteries. In well-developed arteries, the majority of SMCs turn into the contractile and quiescent phenotype. However, after metabolic or physical injuries, those SMCs differentiate into the "activated phenotype". Just after the arterial injury, the SMCs can release numerous proteolytic enzymes, including serine- and metallo-proteinases, and can further contribute to the break-down of elastic fibers and lamellae. In the consecutive repair stage, the SMCs respond to numerous signals, including those initiated by the degradation products, and resume intense proliferation, migration and deposition of the new ECM that contains a disproportionally high amount of collagen and scarce and disorganized elastic fibers. Also, during the slow development of atherosclerosis, the outgrowth of activated SMCs is preceded and facilitated by the progressive degradation of the existing elastic fibers that cannot be replaced during the pathological remodeling of arterial walls and formation of the occlusive neointima. Current therapeutic approaches, including balloon angioplasty and implantation of drugs-eluting stents, dramatically improved the outcome of arterial occlusions caused by an overzealous healing process and thrombosis. However, the overall success rate of these life savings techniques is often diminished by the growth of activated SMCs through the stent mesh and the additional production of collagen fibers, and this leads to rigid in-stent stenosis. Heightened migration and proliferation of the tunica media derived SMC coincide with the inhibition of new elastic fibers formation, and that this pathology could be reversed after the stimulation of new elastogenesis, either in vitro or in intra-arterial stents. While the pro-elastogenic action of numerous factors has been documented, the diverse side effects of high concentrations of those factors (TGFβ-1, IGF-1, aldosterone or dexamethasone) limit their chronic use in clinic. This elastogenic potential of low concentrations of SA are useful for methods of preventing pathologic remodeling leading to arterial occlusions, and also useful in conjunction with mineralocorticoid receptor blockers that would inhibit collagenogenesis and enhance beneficial effects of angioplasty and stents implantation. Moreover, SA is also useful for methods of stimulation of elastic fiber production by isolated cells embedded in bioengineered vessel constructs, thereby enhancing the resilience and adaptability of the constructs after implantation to the human arteries.

Cardiac fibroblasts are the most abundant cell type of the myocardium responsible for production of ECM proteins supporting the structure of beating myocardium. However, in metabolically injured or post-infarct hearts, these stromal cells usually respond to numerous hormones and cytokines with the overzealous production of collagen type I, leading to the formation of rigid post-infarct scars and myocardial fibrosis. It has been shown that pharmacological inhibition of proteolytic degradation of myocardial elastic fibers, occurring after cardiac infarction, reduces inflammatory infiltration and cardiac dilatation. Also, it has been documented that blocking of the mineralocorticoid receptors improved diastolic function after myocardial infarction, and lead to a significant decrease of post-infarct mortality. It has also been determined that aldosterone, applied in the presence of mineralocorticoid receptor inhibitors, exclusively stimulates the production of new elastin by the heart stromal fibroblasts, in the mechanism that involves cross-activation of c-Src and consecutive phosphorylation of the IGF-1 receptor, which in turn triggers the downstream elastogenic pathway. The observation that micromolar concentrations of SA also activates c-Src, phosphorylation of IGF-1 receptor, and successive propagation of the downstream elastogenic pathway, indicates that SA is also useful in methods of treatment of post-infarct patients, especially in view of the observations that the simultaneous application of SA with inhibitors of mineralocorticoid receptors, or with inhibitor of proline hydroxylase, allowed for the exclusive up-regulation of the net elastic fibers deposition by cultured AoSMC and fibroblasts derived from human heart. The addition of SA to the already accepted treatments with eplerenone or spironolactone that prevent aldosterone-induced collagenogenesis, is therefore useful to selectively promote formation of the resilient connective tissue framework in the post-infarct myocardium and allow for better compliance with the beating heart.

As such, SA is indicated for the simultaneous stimulation of collagen and elastin in bioengineered constructs of human tissues containing the residential stem and fully differentiated fibroblasts isolated from adult human skin and fat tissue. Likewise, SA is also indicated for application in combination with factors interfering with collagen deposition, for propagation of a non-fibrotic remodeling of the heart, for prevention of arterial stiffness, and for improvement of dermal scarring.

Generally speaking, the term "tissue" refers to any aggregation of similarly specialized cells which are united in the performance of a particular function. As used herein, "tissue," unless otherwise indicated, refers to tissue which includes elastin as part of its necessary structure and/or function. For example, connective tissue which is made up of, among other things, collagen fibrils and elastin fibrils satisfies the definition of "tissue" as used herein. As such, tissue may comprise cells such as skin fibroblasts, fat tissue fibroblasts, myocardium fibroblasts, and smooth muscle cells. These cells can comprise, even partially, a tissue type such as post-infarct cardiac tissue, occluded tissue, dermal scar tissue, traumatically injured tissue and chronic wounds, for example.

Additionally, elastin is involved in the proper function of blood vessels, veins, and arteries in their inherent viscoelasticity.

For example, in some aspects, the invention is directed to a pharmaceutical composition comprising a compound, as defined above, and a pharmaceutically acceptable carrier or diluent, or an effective amount of a pharmaceutical composition comprising a compound as defined above.

The compounds of the present invention can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the compounds of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

Pharmaceutical formulations containing the compounds of the present invention and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics,* 6th Edition, MacMillan Publishing Co., New York (1980) can be consulted.

The compounds of the present invention can be formulated for parenteral administration by injection, e.g., by bolus injection or continuous infusion. The compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present invention can also be formulated in rectal compositions such as suppositories or retention enemas, e.g., containing conventional suppository bases such as cocoa butter or other glycerides.

In addition to the formulations described previously, the compounds of the present invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the present invention, for example, can be applied to a plaster, or can be applied by transdermal, therapeutic systems that are consequently supplied to the organism.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compounds of the present invention can also be administered in combination with other active ingredients, such as, for example, adjuvants, protease inhibitors, or other compatible drugs or compounds where such combination is seen to be desirable or advantageous in achieving the desired effects of the methods described herein.

The extracellular matrix (ECM) is a complex network of proteins and carbohydrates that provide the framework and physical support for structural organization of practically all tissues and organs. The ECM is made up of fibronectin, laminin, collagen and elastic fibers, as well as numerous glycosaminoglycans and protoglycans. These ECM components are organized into a network of rope-like structures which underlies many tissues, such as, blood vessels, skin, tendons, ligaments, and lungs. Of these components, the major fibrotic components that provide tissues with mechanical strength and resiliency, are the collagen and elastic fibers, respectively. The elastic fibers are composed of two major components: an amorphous, elastin core which makes up the bulk (>90%) of the fiber; and the 10-12 nm microfibrilary component surrounding the elastin core, and made up of glycoproteins, such as, for example, fibrillins, fibulins and microfibril-associated glycoproteins (MAGPs).

Elastin is unique in that it can be stretched to over 150 percent of its original length and rapidly returns to its original size and shape. This property provides tissues in which elastin is incorporated, with the ability to resume their original form after stretching. Therefore, elastin and elastin fibers provide these tissues with the ability to maintain their resiliency, stretchability, and shape. Elastin may also be interwoven with non-elastic collagen fibers to limit stretching and prevent tearing of certain tissues. Mature (insoluble) elastin is metabolically inert and remains the most durable element of extracellular matrix. In undisturbed tissues, mature elastin may last for the lifetime of the tissue Elastic fiber formation, or elastogenesis, is a complex process involving intracellular and extracellular events. Cells such as fibroblasts, endothelial cells, chondroblasts or vascular smooth muscle cells, first synthesize and secrete glycoproteins that form a microfibrillilar scaffold into the extracellular space. Tropoelastin, the soluble precursor peptide of elastin, is synthesized in these cells by ribosomes in the rough endoplasmatic reticulum, and is transported through the Golgi apparatus and secretory vesicles that deposit tropoelastin in the extracellular space. Once outside the cell, tropoelastin is assembled into long chains and covalently cross-linked by lysyl oxidase. During crosslinking, unique composite amino acids, desmosine and isodesmosine, which join the tropoelastin chains, are formed and insoluble elastin is created.

Deposition of elastin in the ECM appears to be controlled on both the transcriptional level (tropoelastin mRNA message expression) and post-transcriptional level (tropoelastin message stability). Other post-transcriptional events which control secretion of tropoelastin monomers, extracellular assembly of tropoelastin, and regulation of cross-linking of tropoelastin may also control elastin deposition.

As the major components of dermal extracellular matrix, collagen- and elastic fibers provide skin with mechanical strength and resiliency, respectively. Elastic fibers are composed of a microfibrillar scaffold containing several glycoproteins and a core of elastin made of cross-linked tropoelastin. Elastic fibers are mainly produced during the second half of foetal development and in early childhood. They do not undergo any extensive turnover and are supposed to last one's lifetime. However, aging and other cellular processes determined by a combination of genetics and environmental factors as well as local inflammation, cause activation of diverse proteases and consequent loss of skin elasticity. Numerous pathological conditions can also contribute to the degradation of the elastic fibers. Elastic fibers cannot be repaired, and once damaged, they have to be replaced by the new ones. The extensive loss of elastic fibers contributes to formation of skin wrinkles, development of arterial aneurysms and lung emphysema, and deterioration of ligaments strength. The extensive loss of elastic fibers clearly contributes to the formation of wrinkles and stretch marks because they cannot be spontaneously repaired or adequately replaced. Although new ECM produced during the healing of dermal wounds contains a small amount of elastic fibers, hypertrophic scars and keloids practically do not contain elastic fibers.

Furthermore, the proper mechanical performance of the myocardium depends on the contractile properties of cardiac myocytes that are supported by the mechanical strength and resiliency of the ECM. Following myocardial injury, the cardiac ECM undergoes dynamic local remodeling, and the insufficient production of elastic fibers, along with an excess of collagen production during the remodeling of a metabolically injured or ischemic myocardium, leads to the production of scar tissue and interferes with the contractility of the myocardium.

The inhibition of elastogenesis in injured arteries, lung and skin tissues can also lead to their development of maladaptive fibrosis and functional impairments.

Recent advances in tissue engineering, utilizing different types of human stem cells, or fully differentiated fibroblasts, chondroblasts or smooth muscle cells embedded into artificial scaffolds, allow for repair and reconstruction of underdeveloped, injured or metabolically damaged human tissues. However, knowledge about endogenous and exogenous factors that can selectively trigger or inhibit production of particular components of the ECM is still limited. Thus, exploration of safe pharmacological interventions that would control the well-balanced production of ECM or particularly stimulate the new elastogenesis by fibroblasts or smooth muscle cells, emerges as a real necessity in regenerative medicine. The selective stimulation of elastic fibers production seems to be particularly needed for the repair of injured heart and lungs, as well as the production of artificial constructs of arteries, heart valves, bladders, and skin substitutes made of human cells placed on biodegradable polymers.

It has been established that the initiation of the elastin gene transcription can be positively regulated by such endogenous factors as glucocorticoids, IGF-1, insulin, TGF-β, and aldosterone. In contrast, tumor necrosis factor-α, interleukin-1β, basic fibroblast growth factor, and Vitamin D3 have been shown to down-regulate elastin gene expression. Currently, only few exogenous factors, such as dexamethasone, retinoids, or ferric ions, have been proven as stimulators of a net elastogenesis. L-ascorbic acid (AA), a potent stimulator of collagen production, has also been listed as an inhibitor of elastin deposition. It has been suggested that AA may destabilize tropoelastin mRNA (and cause overwhelmed hydroxylation on prolyl/lysyl residues of tropoelastin molecules, thereby promoting their accumulation inside cells and inhibiting their secretion.

Embodiments of the invention show that micromolar concentrations of SA stimulate production of both collagen and elastic fibers by cultured human fibroblasts derived from normal and elastin-deficient tissues, as well as by vascular smooth muscle cells.

Further embodiments, though not bound by theory, present a mechanistic explanation of the elastogenic effects of such concentrations of SA.

One embodiment of the invention provides a method for stimulating production of elastic fiber by cells capable of producing the elastic fiber, the method comprises administering an effective amount of sodium ascorbate to the cells.

A further embodiment provides a method wherein the cells comprises at least one of fibroblasts and smooth muscle cells.

A still further embodiment provides a method wherein the cells comprise one or more of the following, skin fibroblasts, fat tissue fibroblasts, myocardium fibroblasts, and arterial smooth muscle cells.

Another further embodiment provides a method wherein the effective amount of sodium ascorbate is between about 50-200 µM sodium ascorbate.

Another further embodiment provides a method wherein production of collagen is stimulated.

Another further embodiment provides a method further comprising administering an effective amount of at least one inhibitor of collagen deposition.

Another further embodiment provides a method wherein the at least one inhibitor of collagen deposition comprises at least one of a proline-hydroxylase inhibitor, and a mineralocorticosteroid receptors inhibitor.

Another further embodiment provides a method of improving the appearance of skin of a subject, the method comprising administering an effective amount of SA to the subject.

Another further embodiment provides a method wherein the SA is administered topically.

Another further embodiment provides a method wherein improving the appearance of skin comprises at least one of decreasing wrinkles, decreasing stretch marks, and decreasing scarring.

Another further embodiment provides a method of decreasing or preventing scar formation, the method comprising administering an affective amount of SA.

Another further embodiment provides a method wherein the scar formation is selected from post-infarct cardiac tissue, arterial occlusions, dermal scars, and injured tissue.

This invention and embodiments illustrating the method and materials used may be further understood by reference to the following non-limiting example.

EXAMPLES

The following provides a listing of at least the primary materials used herein, and sources thereof. In all described experiments the following was used: (+)-sodium L-ascorbate (CAS 134-03-2) from Sigma-Aldrich (St. Louis, Mo.) prepared in a form of 99.0% pure powder suitable for cell culture (A4034). However, in several pilot experiments we also tested a preparation of SA from Santa Cruz Biotechnology, Inc. (Santa Cruz, Calif.) (sc-215877) and found that both SA preparations obtained from different sources produced comparable results. All other chemical-grade reagents, L-ascorbic acid, human insulin, human IGF-I, inhibitor of IGF-1 receptor-I PPP, and inhibitor of C-Src kinse PP2 were from Sigma-Aldrich (St. Louis, Mo.). Probenecid was from ICN Biomedicals Inc. (Aurora, Ohio). The prolyl hydroxylase inhibitor, DMOG, was from Cayman Chemical (Ann Arbor, Mich.). The aldosterone synthetase inhibitor, 4-fluoro-N-(3-pyridin-3-yl) benzamide, was from Chem Div, Inc. (San Diego, Calif.). The DMEM, FBS and other cell culture products were acquired from GIBCO Life Technologies (Burlington, ON.

Biopsies and Experimental Design—The approval from the Medical Ethical Review Board and patient informed consents were obtained for all described studies that used small fragments of skin excess collected during plastic surgery procedures. Guidelines for the protection of human subjects of the Department of Health and Human Services and of the Declaration of Helsinki Principles were followed in obtaining tissues for this investigation. In all described experiments, skin biopsies were derived from 6 normal females, 6 patients with stretch-marked skin, and 5 patients with abdominal hypertrophic scars. All donors were 25- to 37-year-old Caucasian females. In all biochemical studies, quadruplicate samples derived from each experimental group were assayed in three separate experiments. Mean and standard deviations (SD) were calculated for each experimental group, and statistical analyses were carried out by ANOVA, followed by Bonferroni's test comparing selected groups, or by t-test, as appropriate. P value of less than 0.05 was considered significant.

Cell Cultures—Fibroblasts initially grew out from the explants of these full thickness skin biopsies and were maintained. The primary cultures of fat-derived fibroblasts obtained from Thermogenesis (Rancho Cordova, Calif.) were also tested. In all described experiments, 2-4 passages of both kinds of fibroblasts were used. In experiments aimed at assessing ECM production, cells were initially plated at a concentration of 100,000 cells/dish. Confluent cultures were then maintained either in serum-free medium (DMEM) or in medium supplemented with 5% FBS in the presence of different reagents that were added 1 hour before treatments with SA.

Immuno-staining—All cultures maintained in the presence and absence of indicated reagents were either fixed in cold 100% methanol at −20° C. (for detection of elastin) or in 4% paraformaldehyde at room temperature (for detection of collagen I). The multiple parallel cultures were then incubated with 10 µg/ml of polyclonal antibody to tropoelastin (Elastin Products, Owensville, Mich.), or polyclonal antibody to collagen type I (Chemicon, Temecula, Calif.). Cultures were then incubated with the respective fluorescein-conjugated goat anti-rabbit, goat anti-mouse, or rabbit anti-goat secondary antibodies. Nuclei were counterstained with propidium iodide (Sigma, Sigma, St. Louis, Mo.). All of the cultures were then examined with a Nikon Eclipse E1000 microscope attached to a cooled CCD camera (QImaging, Retiga EX) and analyzed by the computer-generated morphometric analysis system (Image-Pro Plus software, Media Cybernetics, Silver Springs, Md.) as previously described.

Quantitative Assays of Insoluble Elastin—Fibroblasts were grown to confluency in 35-mm culture dishes (100,000 cells/dish). Next, 2 µCi of [3H]-valine/ml (Amersham Biosciences Ltd. Oakville, Canada), were added to each dish along with or without the indicated treatments. At the end of each experiment, the levels of metabolically labeled NaOH-insoluble elastin present in individual cultures were assayed and normalized per their DNA content.

Organ culture of skin explants—Fragments of normal skin, stretch-marked skin and dermal scars collected during plastic surgery procedures were cut into multiple 4 mm2 pieces and maintained for 7 days in DMEM medium containing 5% FBS, in the presence or absence of 200 µM SA alone or in combination with 200 µM DMOG as described in figure legends. The parallel quadruplicate explants from each experimental group were additionally maintained in the presence 2 µCi of [3H]-valine/ml and then subjected to the assay of insoluble elastin. The parallel explants from each experimental groups were also evaluated after pentachrome Movat's staining which allows for clear marking of elastic fibers. In each experimental group, 50 sections derived from quadruplicate explants were analyzed.

One-Step RT-PCR Analysis—The confluent cultures of skin fibroblasts were treated with or without the reagents of interest for different periods of time as indicated in the figure legend. Total RNA was extracted using the RNeasy Mini Kit, and the one-step RT-PCR reactions were set up with the RT-PCR Kit, according to the manufacturer's (Qiagen, Mississauga, ON) instructions. The amounts of tropoelastin mRNA were always normalized to the amount of GAPDH mRNA.

Western Blots—At the end of indicated experiments, cells were lysed with NP-40 buffer containing a cocktail of broad spectrum inhibitors of proteinases and phosphatases. The 50 µg aliquots of protein extract were then resolved by SDS-PAGE gel (4-12% gradient) in reducing conditions and analyzed by Western blot with antibodies indicated in figure legends, as previously described. Initial blots were also re-probed with monoclonal anti-β-actin antibody (Cell Signaling Technology Inc., Danvers, Mass.) to confirm the equal protein loading. The degree of expression was measured by densitometry.

Immuno-precipitation—To evaluate the levels of IGF-I receptor or insulin receptor phosphorylation, cultures maintained either in serum-free medium or in medium with 2% FBS were incubated for 15 minutes in the presence or absence of 100 µM SA or 50 ng/ml IGF-1 with or without 30-minute pretreatment with 0.5 µM PPP or 10 µM PP2. At the end of each experiment cells were submerged in the lysis buffer containing a broad-range phosphatase inhibitor. The polyclonal antibodies recognizing either the β subunits of the IGF-IR or the β subunit of the insulin receptor were immobilized on separate sets of the IgG-bearing magnetic beads (Invitrogen Canada Inc, Burlington, ON) and then incubated for 1 hour with the aliquots of the cell lysates containing 400 µg of protein as described in the manufacturer protocol. The beads bearing the resulting immuno-precipitation products were re-suspended in sample buffer and the released proteins were resolved with SDS-PAGE and subjected to Western blotting with a monoclonal anti-p-Tyr (PY99) antibody from Santa Cruz Biotechnology Inc. (Santa Cruz, Calif.) and then with HRP-conjugated goat anti-mouse secondary antibody.

Quantification of Intracellular free radicals-reactive oxygen species (ROS)—To assess the levels of ROS, quadruplicate cultures of normal skin fibroblasts were exposed to 10 µM of ROS-sensitive CM-H2DCFDA fluorescent probe (Molecular Probes, Eugene, Oreg.) for 30 minutes. This probe passively diffuses into the cell interior and only upon oxidation is a fluorescent product released that can be visualized under a fluorescent microscope or captured by flow cytophotometry when excited at 480 nm. Fibroblasts were then maintained for 30 minutes in the presence or absence of 400 µM probenecid, then incubated either for 2 or 24 hours with and without 100 µM AA or 100 µM SA. At the end of these periods the images were captured using a fluorescent microscope under identical parameters of contrast and brightness. The ROS production was also assessed by flow cytophotometry ($\lambda$ excitation 480 nm; $\lambda$ emission 520 nm), using FACSCalibur, Beckton Dickinson Instrument.

Example 1

SA induces the deposition of elastic fibers in monolayer cultures of human skin-derived fibroblasts.

Figure 1B:
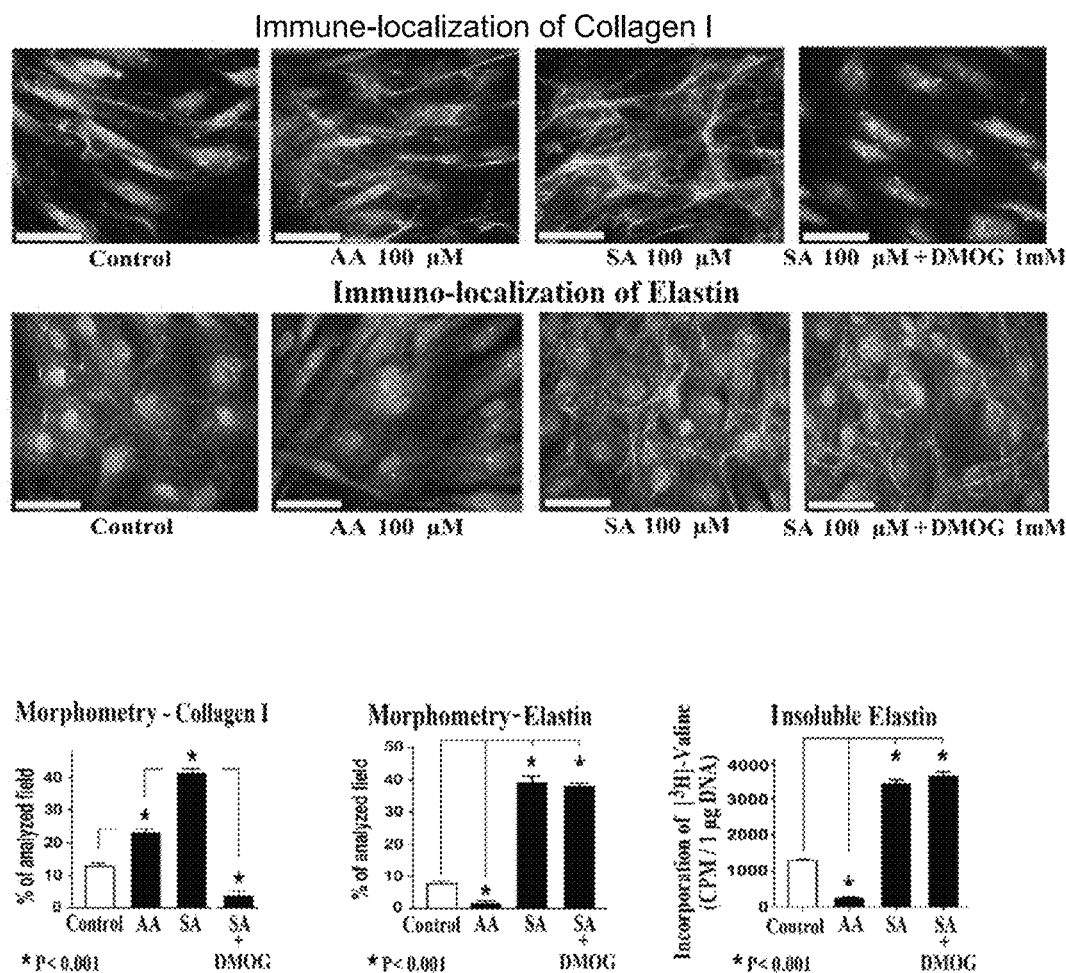

It was found that small concentrations of SA, ranging from 50 µM to 200 µM, significantly stimulated production of immuno-detectable elastic fibers in 24-hour-old cultures of normal dermal fibroblasts. In contrast, higher concentrations of SA did not further stimulate deposition of elastic fibers (400 µM), and even induced a clear inhibition of elastogenesis (800 µM SA). Meaningfully, it was also established that treatments of parallel cultures, either with 100-200 µM NaCl or with a mixture of 100 µM of NaCl and 100 µM of AA, did not cause any up-regulation in elastic fiber deposition (FIG. 1A, upper panels). Moreover, treatment with 100 µM AA alone stimulated collagen deposition by cultured fibroblasts, but completely inhibited their elastogenesis. While causing remarkable up-regulation in the net deposition of new elastic fibers, treatment with 100 µM SA also induced a more potent up-regulation in the deposition of immuno-detected collagen fibers than 100 µM AA (FIG. 1B, upper panels). It has been established that addition of the prolyl hydroxylase inhibitor DMOG along with 100 µM SA to cultured fibroblasts inhibited the deposition of collagen fibers, but did not interfere with the enhanced production of elastic fibers. All mentioned results based on morphometric evaluations of the immuno-detected elastic fibers correlated well with results from the quantitative assay of metabolically labeled insoluble elastin performed on parallel cultures (FIGS. 1A-1B, lower panels).

Example 2

SA also enhances deposition of collagen and elastin by cultured fibroblasts derived from dermal fat.

The morphometric evaluations of immuno-staining along with the quantitative assay of metabolically labeled insoluble elastin in parallel cultures of fat tissue-derived fibroblasts indicated that a similar concentration of SA (50-200 µM) induced, on average, a 22%+/−4% increase in elastin deposition ($p<0.01$) in cultures of fibroblasts isolated from dermal human fat tissue.

Example 3

Inhibition of the sodium-dependent vitamin C transporters eliminates SA-induced elastogenesis.

The cellular mechanism by which SA stimulates production of elastic fibers was initially demonstrated by the addition of 50-200 µM of SA causing a significant and dose-dependent up-regulation of the levels of tropoelastin-encoding mRNA (detected by RT PCR) 18 hours after its addition to cultures maintained in medium supplemented with 5% FBS. This preceded an increase in the levels of newly synthesized tropoelastin (detected by Western blots) in 20-hour-old cultures and in levels of insoluble elastin observed in 24 hour-old cultures. The results of three separate experiments showing the elastogenic potential of 100 µM SA are shown in FIGS. 2A-2D. Since the salt configuration ensures the temporal stability of SA molecules in the culture medium (pH 7.4), cultured skin fibroblasts were also exposed to 400 µM probenecid and it was found that their pre-incubation with this SVCTs inhibitor eliminated the elastogenetic effects of 100 µM SA observed in the amount of message, precursor protein and final product levels (FIGS. 2A-2D). Interestingly, cultures maintained for 24 hours with 100-400 µM probenecid alone did not demonstrate any decrease in their basic deposition of elastic fibers below the level observed in untreated control cultures. Together, the results obtained from three independent experiments indicate that a quick transportation of SA-derived, non-oxidized ascorbate anions into the cell interior may contribute to the enhancement of elastogenesis.

Example 4

Treatment with SA associates with a decrease in levels of intracellular reactive oxygen species (ROS).

Figure 2A:
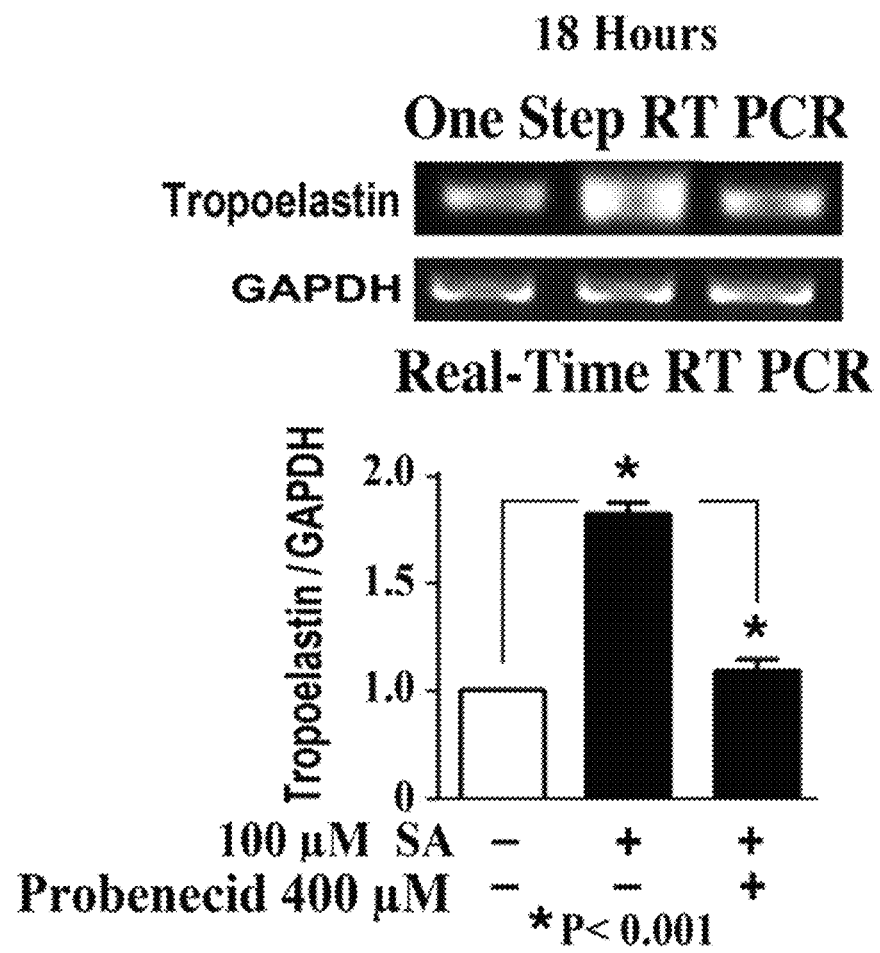
FIGS. 2A-2F. Representative images of one step RT-PCR visualizing of tropoelastin and GAPDH mRNAs correlating with results of quantitative real-time RT-PCR (A), results of the quantitative Western blot-based assessments of intracellular tropoelastin (B) followed by results of quantitative assay of metabolically-labeled insoluble elastin (C) and morphometric evaluations of the immuno-detected elastic fibers (D) demonstrate that probenecid-dependent inhibition of intracellular transport of SA-derived non-oxidized ascorbate anions averts the induction of elastogenic effects observed at indicated times in cultures treated with SA alone. Fibroblasts exposed to the ROS-sensitive fluorescent probe and treated for 2 hours with 100 μM SA contain significantly lower levels of ROS detected by both fluorescence microscope (E) and flow cytometry (F). Exclusion of the fluorescent probe and addition of 0.01% hydrogen peroxide represents the negative and positive control, respectively. This effect of SA could not be observed in cultures in which the intracellular influx of SA has been inhibited by pre-incubation with probenecid. (Scale bars=15 μm). Results (mean±SD) are based on data obtained from three individual experiments, in which quadruplicate cultures were exposed to indicated treatments.
Figure 2B:
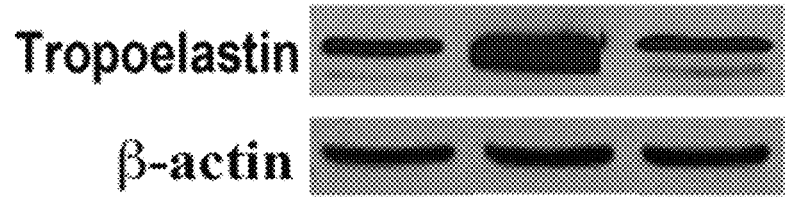
Figure 2B:
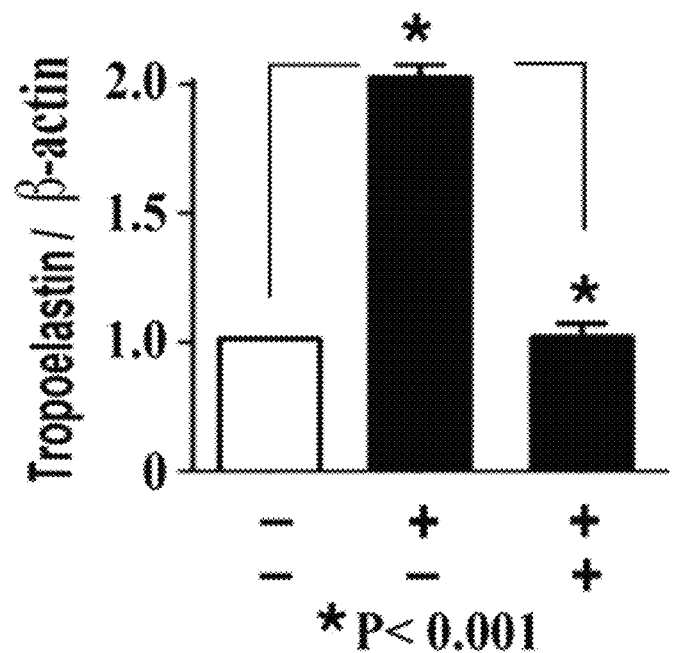
Figure 2C:
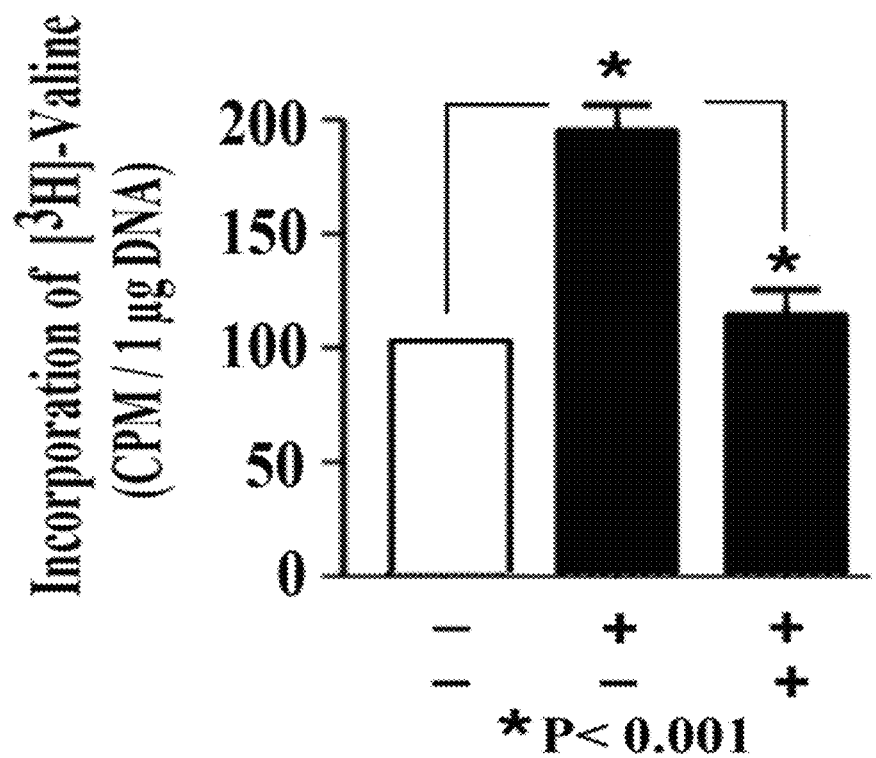
Figure 2D:
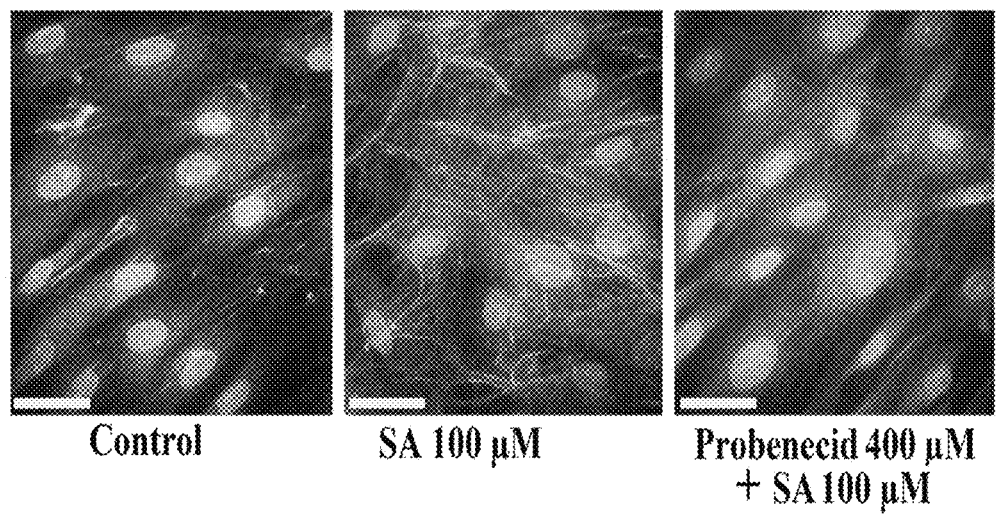
Figure 2D:
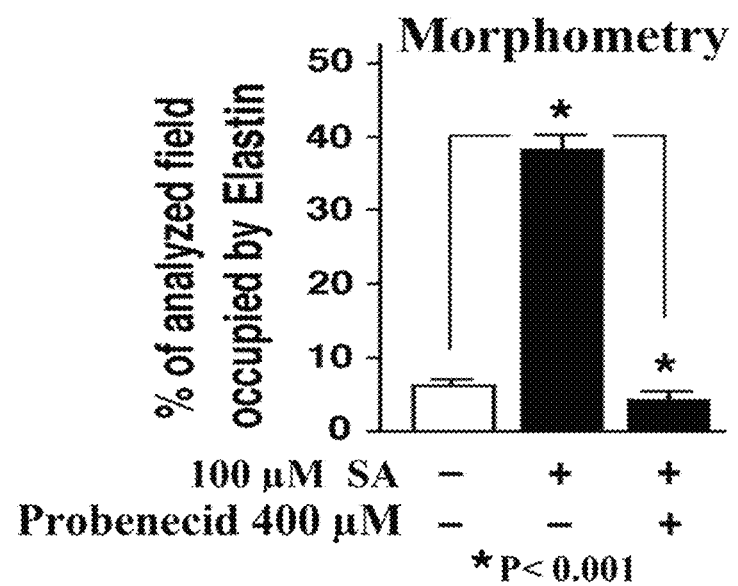
Figure 2E:
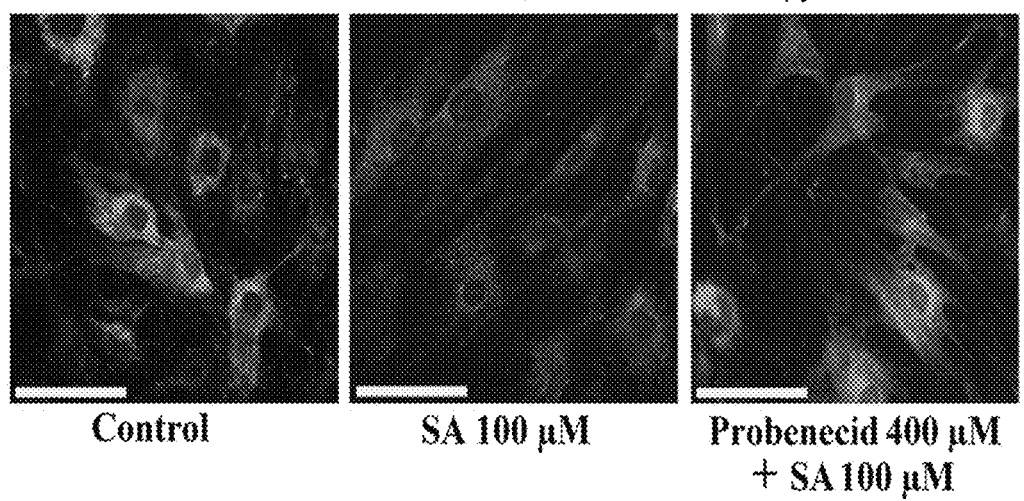
Figure 2F:
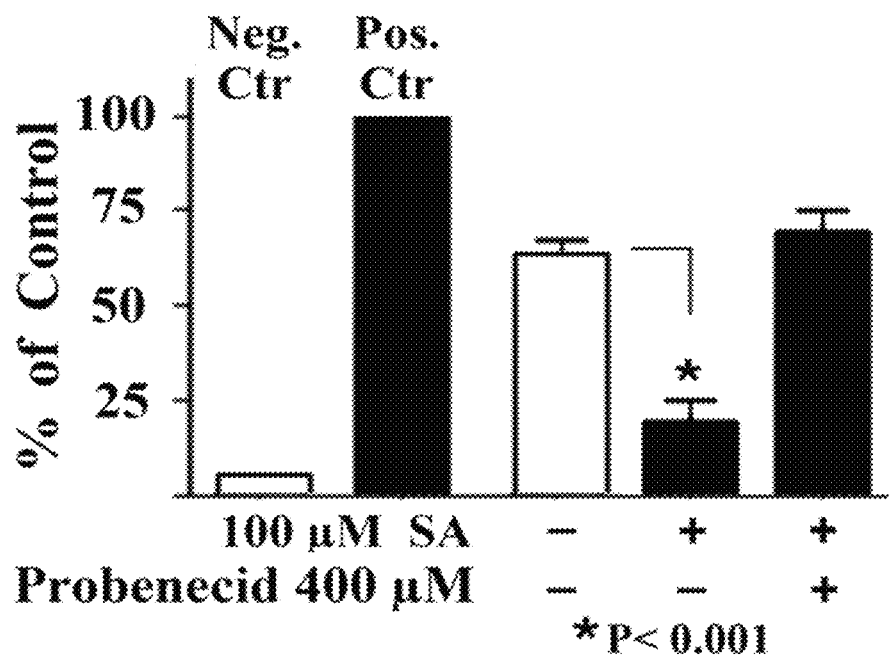

Next, fibroblasts were exposed to the ROS-sensitive fluorescent probe, CM-H2DCFDA and found that cells treated for only 2 hours with 100 µM SA contained significantly lower levels of ROS that could be detected by fluorescence microscope or by the flow cytophotometry (FIGS. 2E and 2F). This effect could not be observed in cultures in which the intracellular influx of SA-derived, non-oxidized ascorbate had been inhibited by pre-incubation with probenecid. The parallel cultures treated for 2 hours with 100 µM AA, did not display any decrease in ROS contents, as compared with untreated counterparts.

Example 5

SA induces enhancement of the primary elastogenic signals triggered by IGF-1 receptor.

Surprisingly, it was also found that the elastogenic effects of SA evident in 18-24 hour-old cultures maintained in the presence of FBS could not be observed in cultures maintained in serum-free medium (FIGS. 3A-3D). This suggested that SA might only enhance elastogenic signals triggered by some other factor(s) present in the serum. Therefore, it was tested whether addition of SA would positively modulate the effects of selected elastogenic stimulators; corticosteroids, TGF-β1 and IGF-1. Results of these experiments indicated that the addition of 100 µM SA did not further enhance the increase in elastogenesis induced by 1 µM dexamethasone or 1 ng/ml of TGF-β1, but significantly up-regulated the levels of elastin deposition induced by 50 ng/ml of IGF-1. Consequently, the putative mechanism by which SA would enhance the IGF-1-induced elastogenic signalling pathway was tested.

Figure 3A:
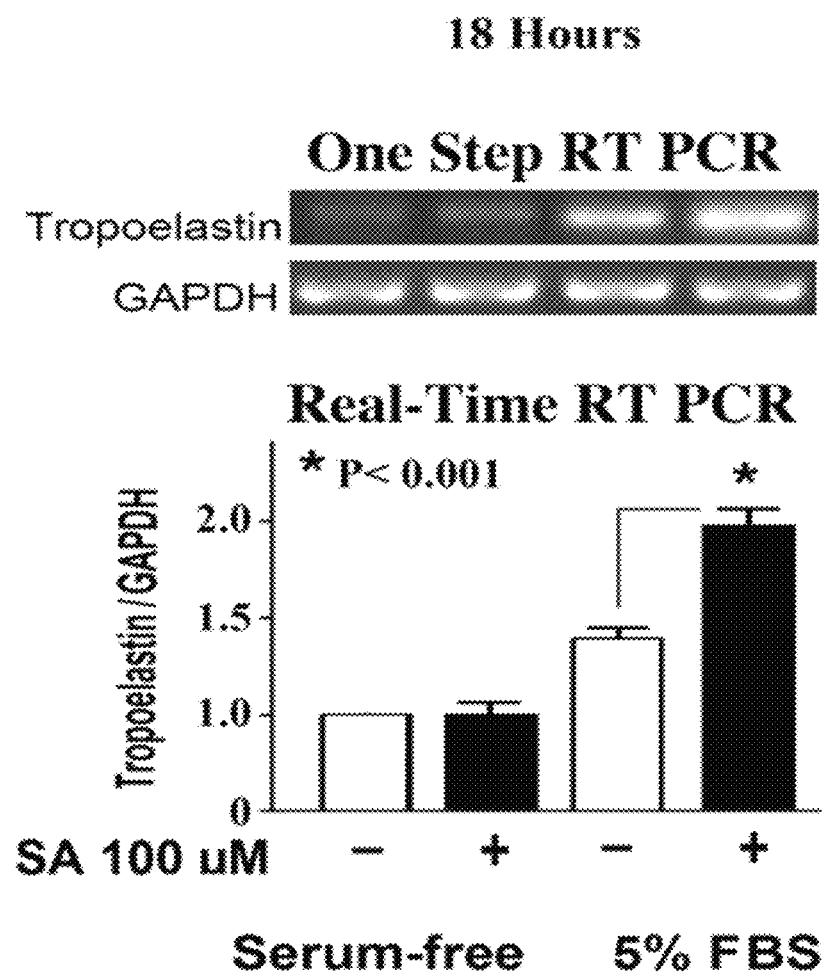
FIGS. 3A-3J. Representative images of one step RT-PCR visualizing tropoelastin and GAPDH mRNAs along with the results of quantitative real-time RT-PCR (A), followed by the results of the quantitative Western blots-based assessments of intracellular tropoelastin (B), the quantitative assay of metabolically-labeled insoluble elastin (C) and representative immuno-fluorescence (D) indicate that 100 μM SA alone upregulates elastogenesis only in cultures of dermal fibroblasts maintained in media containing 5% FBS. (E) Treatment with 100 pM SA alone enhances the level of phosphorylation of the IGF-1R (immuno-precipitated with antibody to β subunit of IGF-1R and detected by Western blotting with anti-phospho-tyrosine antibody) only in cultures maintained in media containing 5% FBS. However, SA enhances levels of IGF-1-induced IGF-IR phosphorylation in both tested media. These SA-induced enhancements of IGF-1R phosphorylation are eliminated in cultures pre-treated with IGF-1 receptor kinase inhibitor (PPP) or with c-Src kinase inhibitor (PP2). (F) In contrast, the treatment with 100 μM SA does not enhance basic or insulin-induced phosphorylation of insulin receptor. (G-J) Preincubations with PP2 or PPP abolish all elastogenic effects that could be observed in indicated times in cultures of dermal fibroblasts treated with IGF-1 and/or SA. Results (mean±SD) are based on data obtained from three individual experiments, in which quadruplicate cultures were exposed to indicated treatments. (scale bars=15 μm).
Figure 3B:
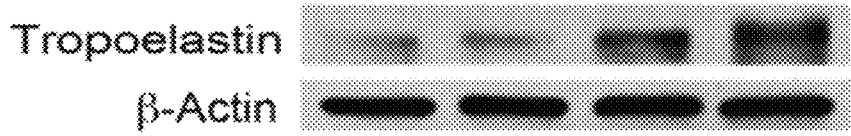
Figure 3B:
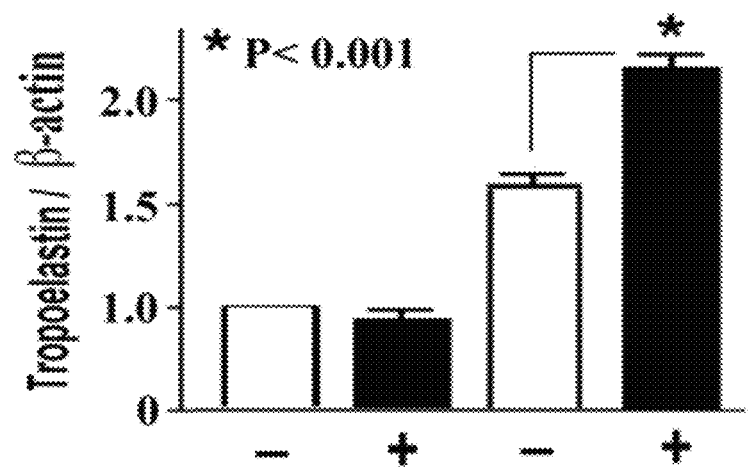
Figure 3C:
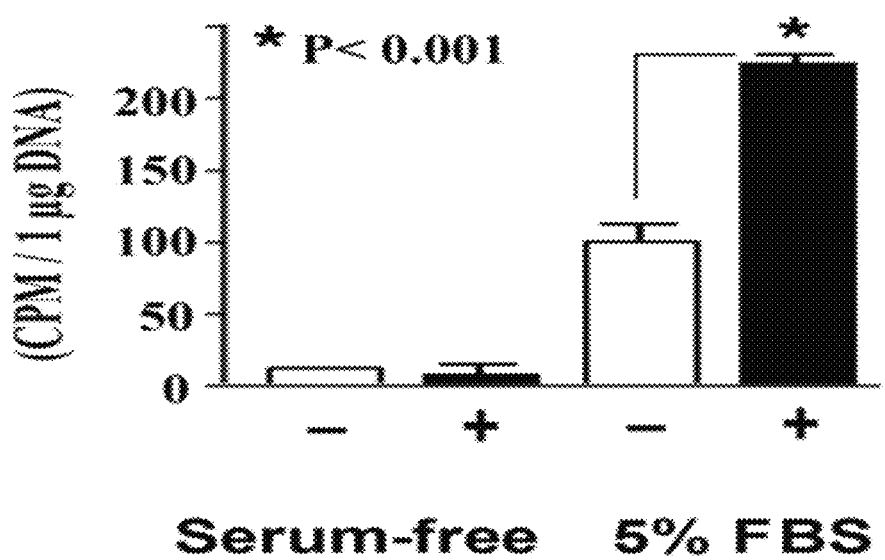
Figure 3D:
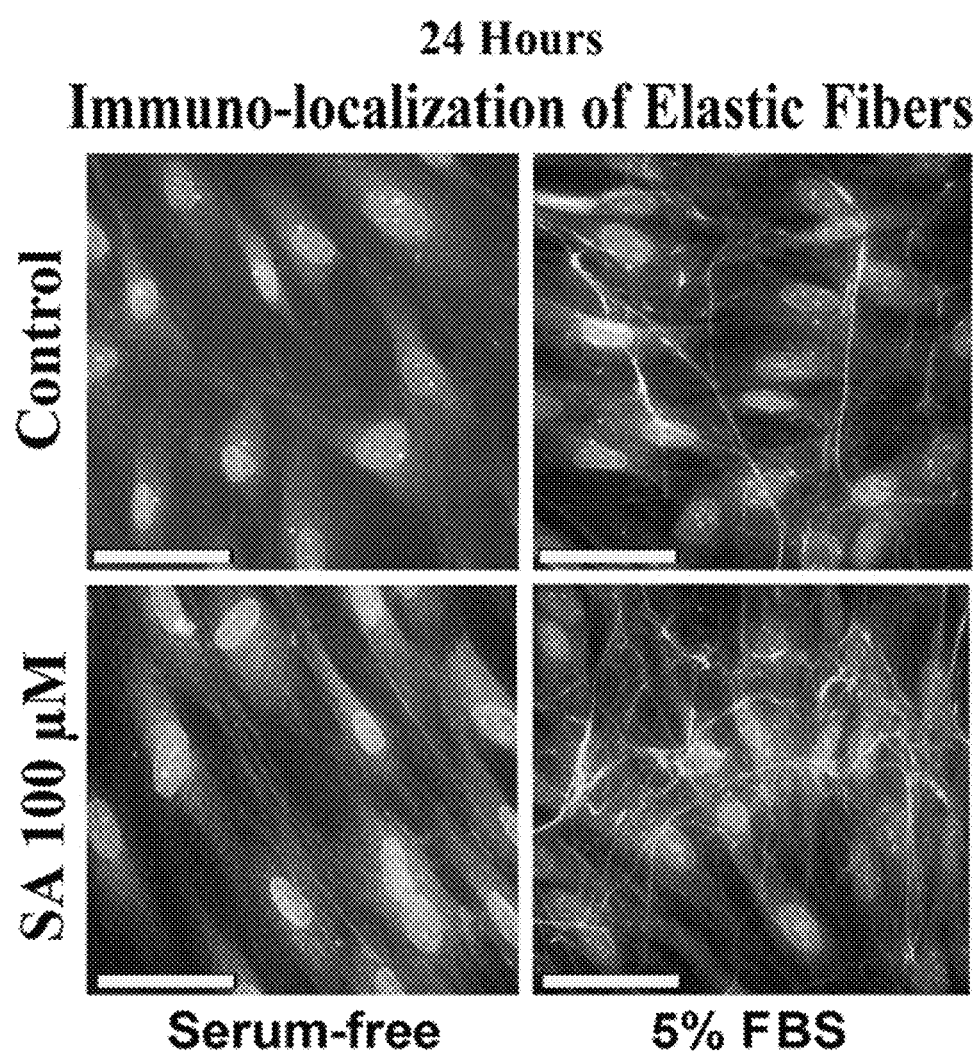
Figure 3E:
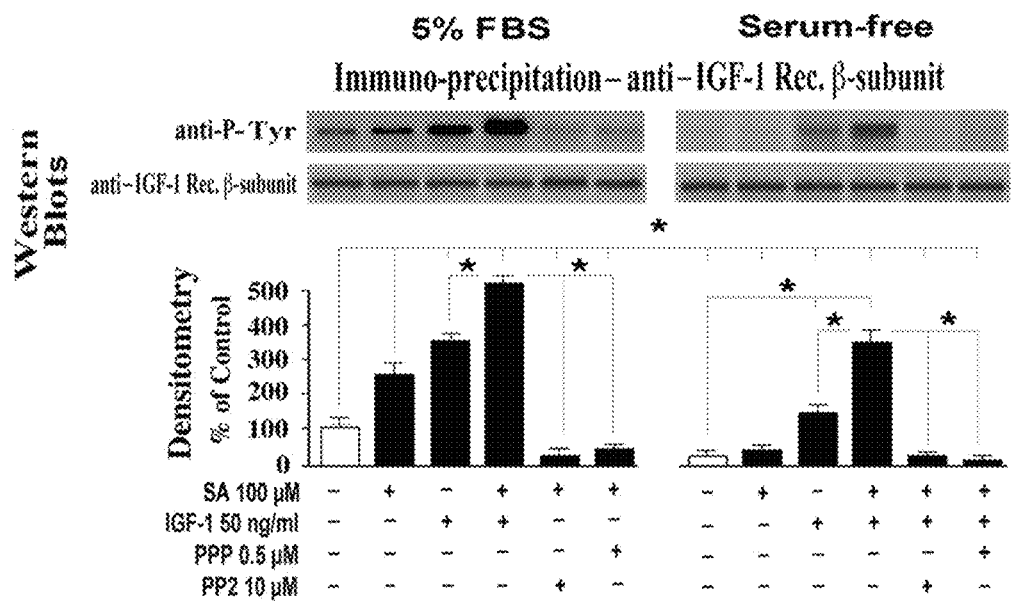
Figure 3F:
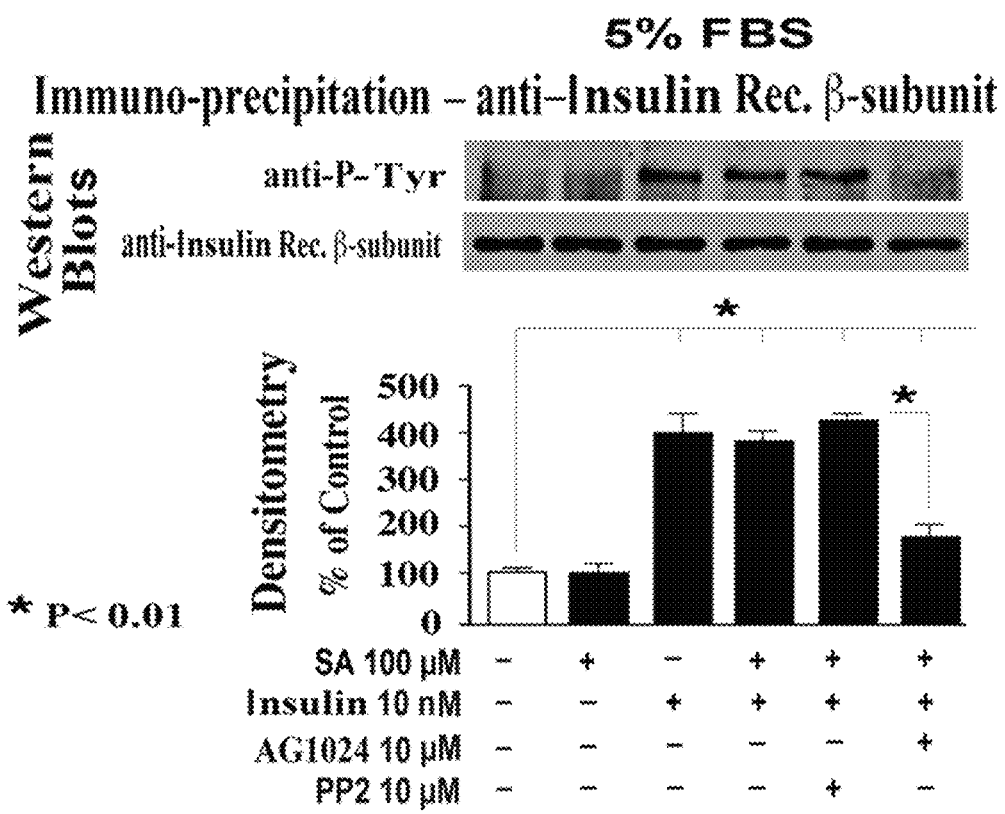
Figure 3G:
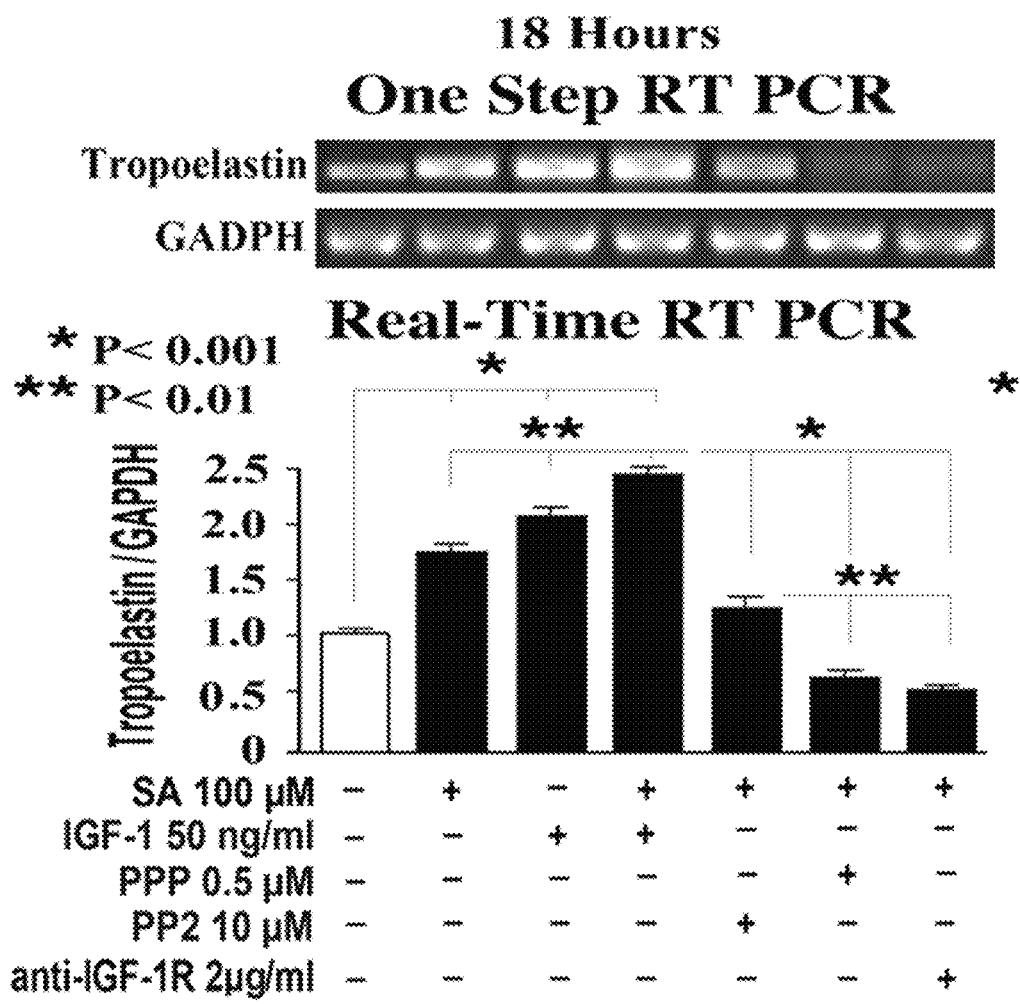
Figure 3H:
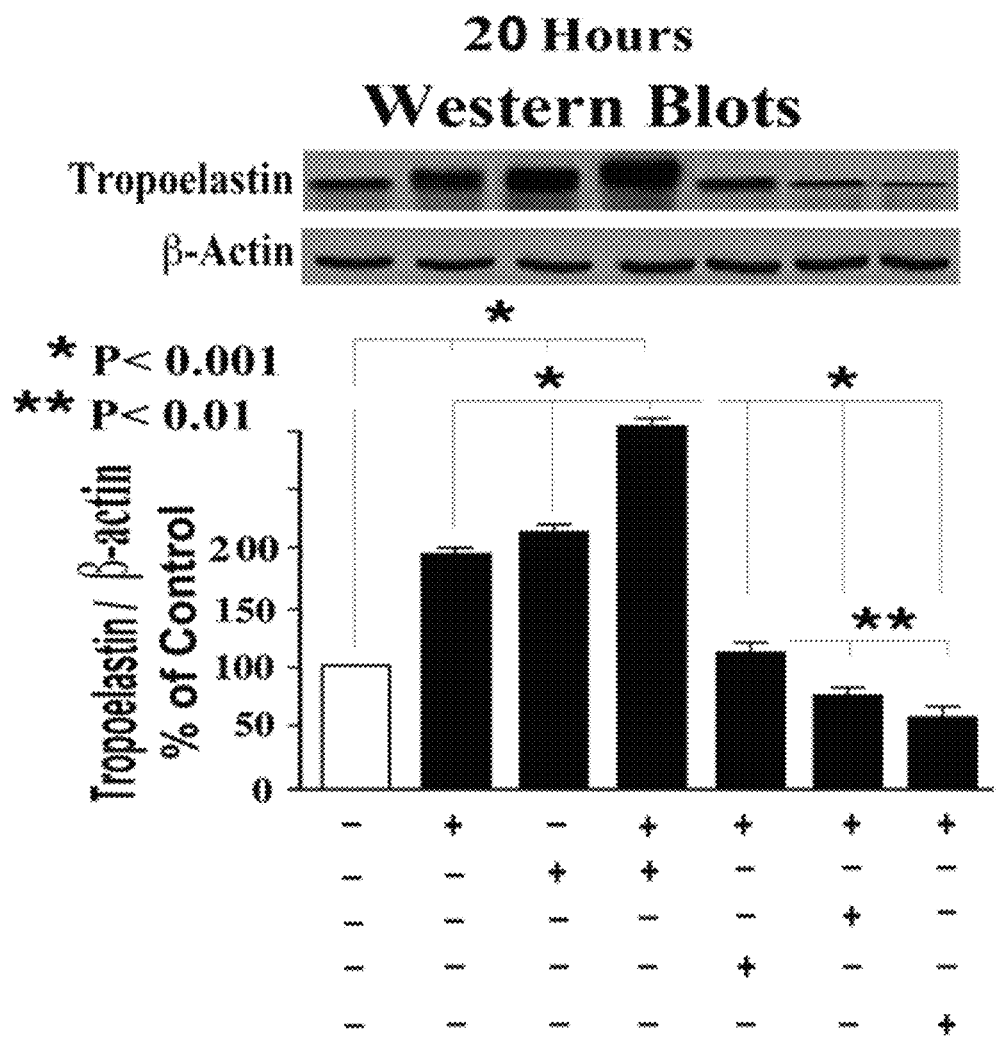
Figure 3I:
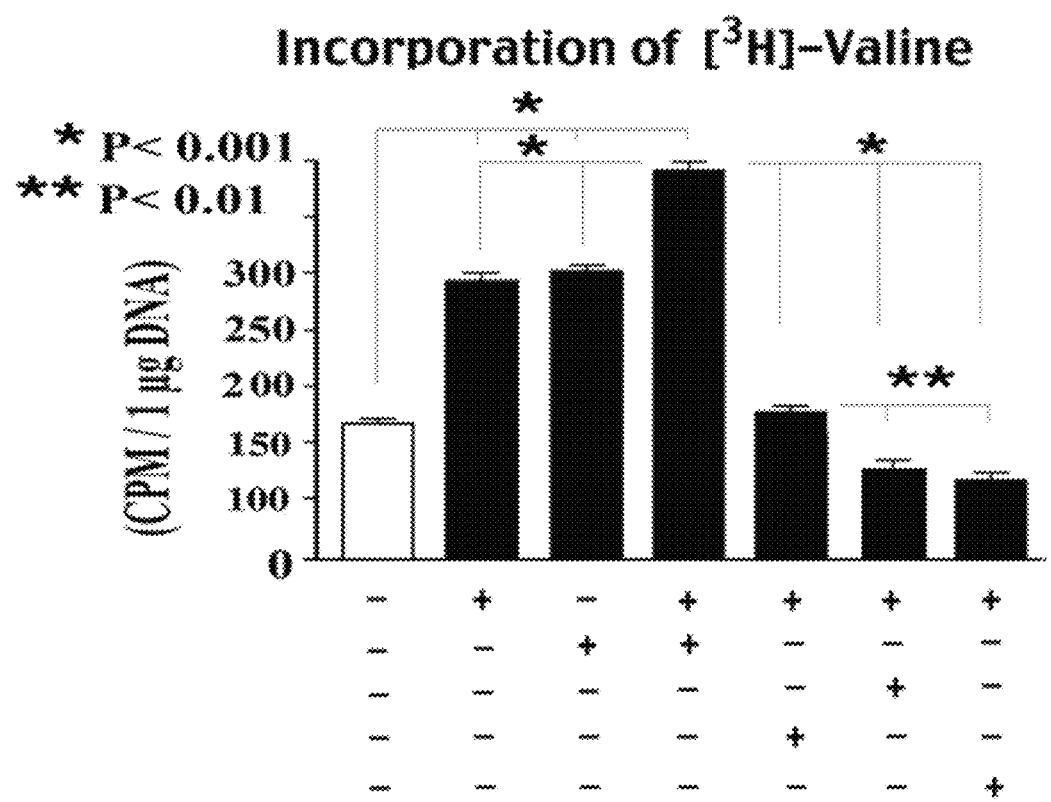
Figure 3J:
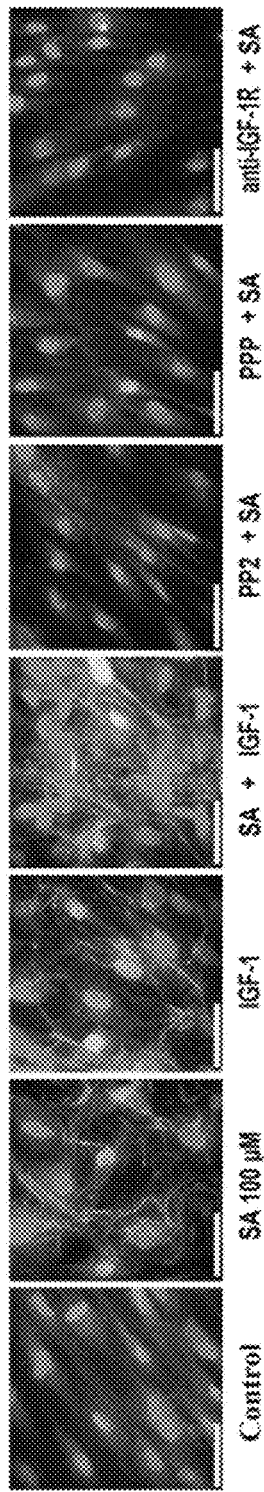

The results of the next experiments (FIG. 3E) revealed that addition of 100 µM SA to fibroblasts maintained in the presence of FBS, remarkably enhanced levels of IGF-1R phosphorylation (immuno-precipitated with antibody recognizing the β subunit of IGF-1R and detected on Western blot with anti-phospho-tyrosine antibody). This was in contrast with fibroblasts maintained in serum-free medium that did not reveal any increase in IGF-1R phosphorylation in response to treatment with the same dose of SA (FIG. 3F). These results suggest that either the presence of SA-derived non-oxidized ascorbate ions enhanced interactions of the extremely small concentration of IGF-1 (2-6 ng/ml of 5% FBS) with IGF-1R or that the independent simultaneous actions of SA and IGF-1 lead to the ultimate enhancement of IGF-1R phosphorylation. The possibility of the super-activation of IGF-1R by a SA-induced cellular mechanism was further endorsed by the fact that additions of 100 µM SA significantly enhanced the levels of phosphorylated IGF-IR in parallel cultures maintained in both tested media treated with 50 ng/ml of IGF-1.

Since this SA-induced enhancement of IGF-1R phosphorylation was eliminated in cultures pretreated and maintained in the presence of either the c-Src kinase inhibitor PP2 or the specific inhibitor of IGF-1R tyrosine kinase PPP, it was concluded that c-Src tyrosine kinase activity is required for the execution of the SA-triggered phosphorylation of IGF-1R. Importantly, SA did not induce heightened phosphorylation of the highly homologous insulin receptors (FIG. 3E). Then, it was found that 24-hour treatment of dermal fibroblasts (maintained in the presence of 5% FBS) with 100 µM SA alone induced a similarly strong elastogenic effects as treatment with 50 ng/ml of exogenous IGF-1. Importantly, parallel cultures jointly treated with IGF-1 and SA displayed even higher levels of tropoelastin mRNA, intracellular tropoelastin, insoluble elastin and immuno-detected elastic fibers than their counterparts treated with either compound on its own. Moreover, SA did not trigger elastogenic effects in cultures pretreated with PP2, PPP or with anti-IGF-1R-blocking antibody (FIGS. 3G-3J). Furthermore, we have also established that inhibition of other kinases contributing to the IGF-1-induced signalling pathway; phosphatidylinositol 3-kinase; (by LY294002) or cyclin-dependent kinase-2 (by CVT313) eliminated elastogenic effects of 100 µM SA.

Example 6

SA ameliorates the poor deposition of collagen and elastic fibers observed in monolayer cultures of dermal fibroblasts and organ cultures of explants derived from dermal stretch marks.

Figure 4A:
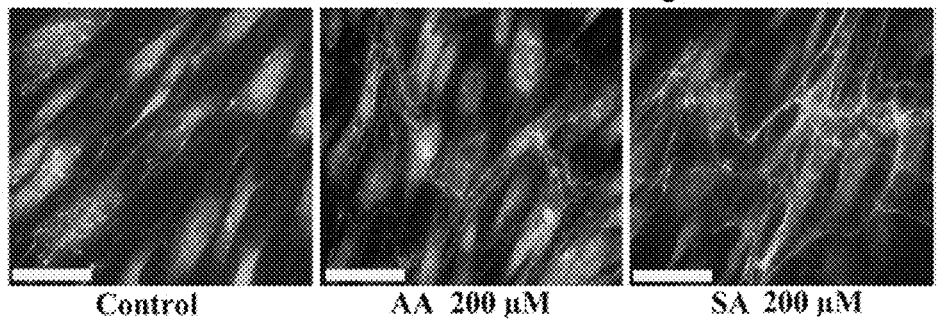
FIGS. 4A-4D. (A) Representative immuno-fluorescence detecting collagen and elastic fibers, their morphometric evaluations, and quantification of the insoluble elastin in 24 hour-old cultures of fibroblasts derived from dermal stretch marks (scale bars=15 μm). Micrographs of Movat-pentachrome-stained sections of dermal explants derived from normal skin (B), dermal stretch marks, (C) and dermal scars (D) cultured for 10-days. (elastin is black, collagen yellow, scale bars=30 μM) accompanied with results of quantitative morphometric evaluations of elastic fibers and quantitative assay of insoluble elastin in all cultured explants show the pro-elastogenic effect of SA. Explants of dermal scars jointly treated with SA and DMOG demonstrate further up-regulation in the deposition of elastic fibers and a decrease in collagen content. Results (mean±SD) are based on data obtained from three experiments utilizing biopsies from 5 individuals, in which quadruplicate cultures were exposed to indicated treatments.
Figure 4A:
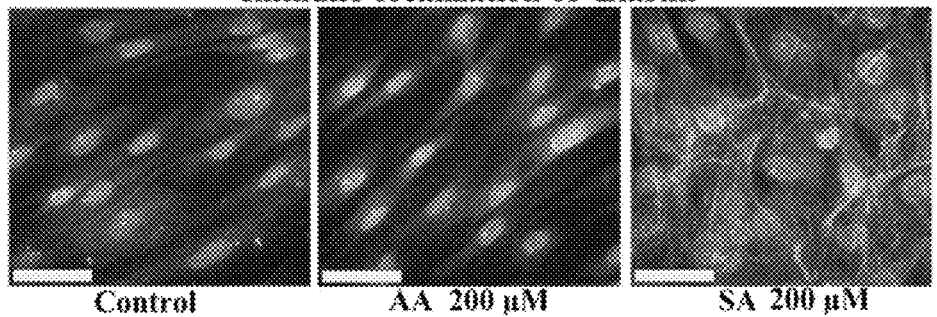
Figure 4A:
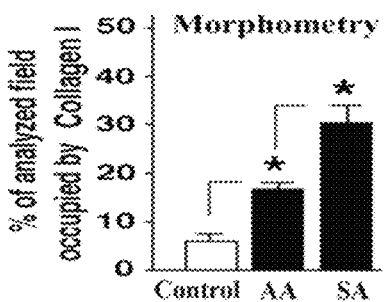
Figure 4A:
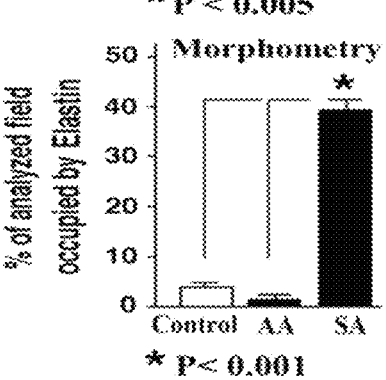
Figure 4A:
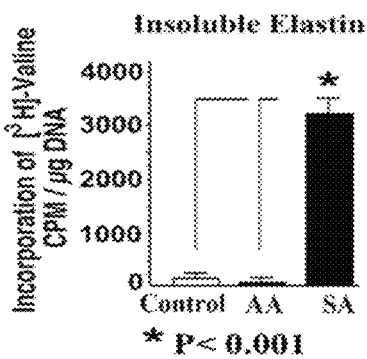
Figure 4B:
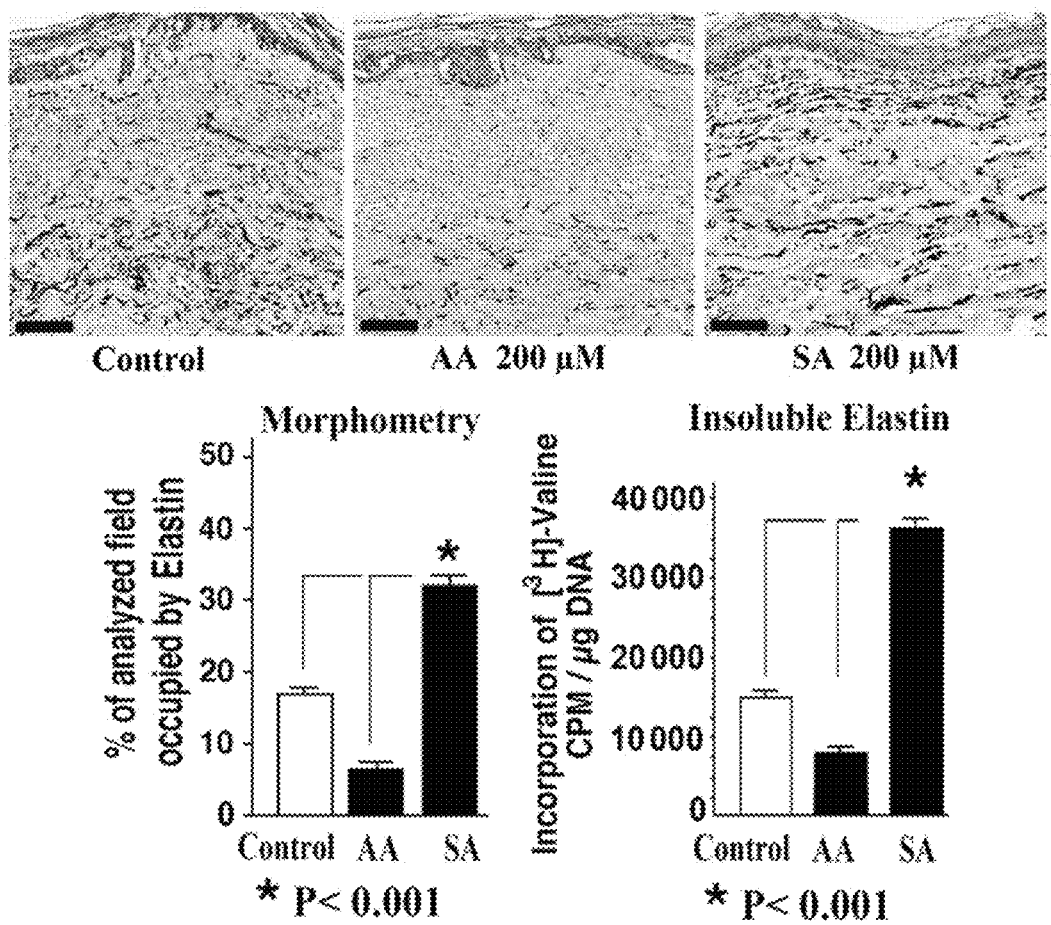
Figure 4C:
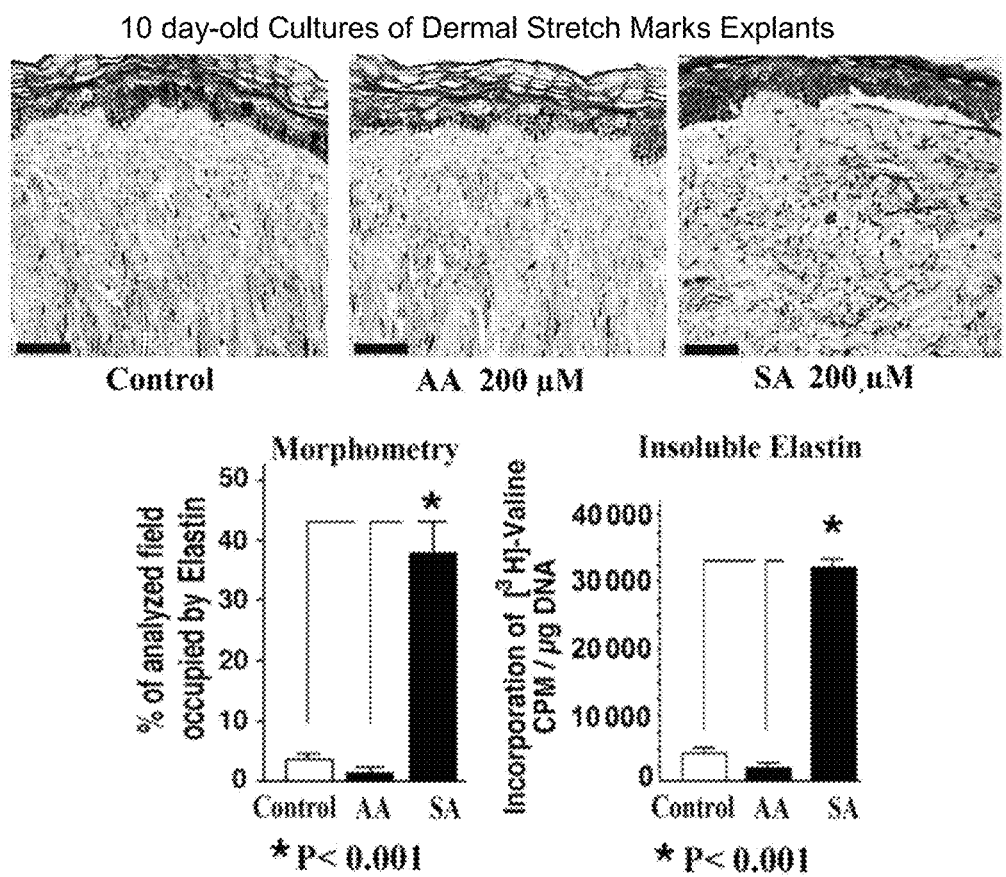

Importantly, it was established that cultured fibroblasts derived from dermal stretch marks also significantly up-regulated their production of both collagen and elastic fibers in response to treatment with 200 µM SA. Also, in this experimental model, the treatment of parallel cultures with 200 µM AA caused a selective inhibition of new elastogenesis (FIG. 4A). The effects of SA in cultured explants of biopsies derived from normal skin and dermal stretch marks was also tested. Results of morphometric analysis of sections stained with pentachrome Movat's method, as well as the quantitative assay of metabolically-libeled insoluble elastin, indicated that the 10-day-long daily treatment with 200 µM SA not only enhanced deposition of new elastic fibers in normal skin explants (FIG. 4B), but restored the practically non-existent elastogenesis observed 10-day-old cultures of full thickness explants of dermal biopsies derived from stretch marks (FIG. 4C). In contrast, parallel explants treated with 200 µM AA demonstrated only up-regulation in the deposition of collagen.

Example 7

SA also induces enhancement of elastic fibers deposition in cultured explants of dermal scars.

Figure 4D:
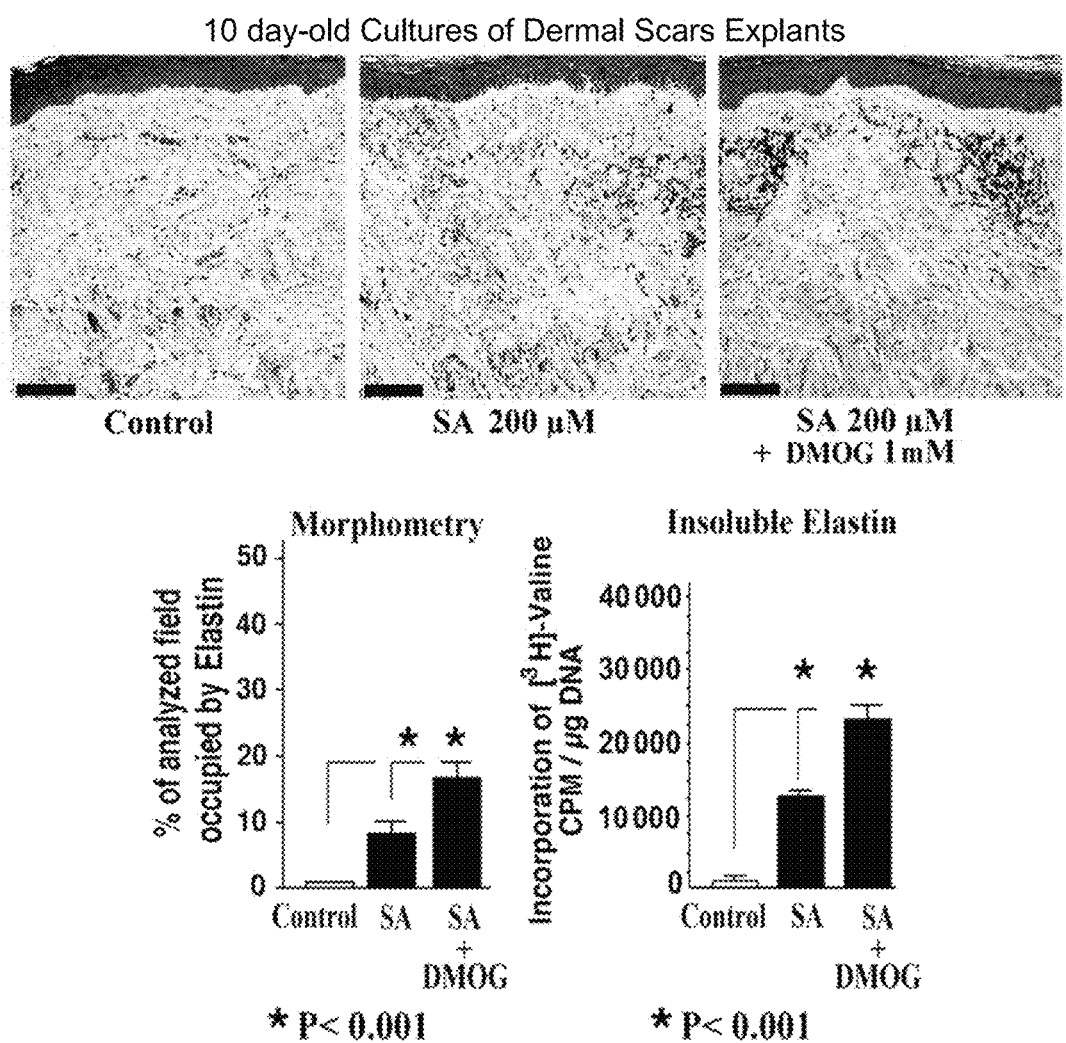

We have also established that treatment with SA induced a beneficial remodelling of cultured explants of the rigid dermal scars. Both histochemistry and quantification of insoluble elastin indicated that treatment with 200 µM SA initiated production of new elastic fibers in their mostly collagenous extracellular matrix. Moreover, we found that explants jointly treated with SA and DMOG, which blocks collagen deposition, demonstrated further up-regulation in the net deposition of elastic fibers (FIG. 4D). Interestingly, parallel scar explants treated with 1 mM DMOG alone did not revealed any elastic fibers in their ECM.

Although the present invention has been described in considerable detail with reference to certain preferred embodiments thereof, other versions are possible. Therefore, the spirit and scope of the appended claims should not be limited to the description and the preferred embodiments disclosed herein.

What is claimed is:

1. A composition comprising an effective amount of an ascorbate salt and an inhibitor of collagen deposition, wherein the ascorbate salt is selected from the group consisting of lithium ascorbate, sodium ascorbate, potassium ascorbate, magnesium ascorbate, calcium ascorbate, and combinations thereof, and
   wherein the inhibitor of collagen deposition is selected from the group consisting of a spironolactone, eplerenone, dimethyloxaloylglycine, and a combination thereof.

2. The composition of claim 1, wherein the ascorbate salt is delivered at a concentration of 50-200 micromolar to a tissue per dose.

3. The composition of claim 1, wherein the inhibitor of collagen deposition is dimethyloxaloylglycine (DMOG).

4. The composition of claim 1, wherein the composition is formulated to be administered by a mode selected from the group consisting of topical, parenteral, subcutaneous, intravenous, intraperitoneal, transdermal, oral, buccal, inhalation, depot injection, and implantation.

5. The composition of claim 1, further comprising a diluent, a filler, a disintegrant, a binder, a lubricant, a surfactant, an emulsifier, a buffer, a humectant, a moisturizer, a solubilizer, a preservative, or a combination thereof.

6. The composition of claim 1, wherein the composition is a solution, a powder, a fluid emulsion, a fluid suspension, an ointment, a paste, a cream, a gel, or a foam.

* * * * *